(12) United States Patent
Lee

(10) Patent No.: US 7,745,199 B2
(45) Date of Patent: Jun. 29, 2010

(54) BACTERIAL CONSORTIUM NBC2000 AND METHOD FOR BIOLOGICALLY TREATING ENDOCRINE DISRUPTERS USING THE NBC2000

(76) Inventor: Sung-gie Lee, Chuncheon Biotechnology Innovation Center No. 314, 198-53, Hupyeong-dong, Chuncheon-city, Gangwon-province, 200-161 (KR)

(*) Notice: Subject to any disclaimer, the term of this patent is extended or adjusted under 35 U.S.C. 154(b) by 787 days.

(21) Appl. No.: 11/587,835

(22) PCT Filed: Apr. 28, 2005

(86) PCT No.: PCT/KR2005/001238
§ 371 (c)(1),
(2), (4) Date: Oct. 26, 2006

(87) PCT Pub. No.: WO2005/105979
PCT Pub. Date: Nov. 10, 2005

(65) Prior Publication Data
US 2008/0248555 A1    Oct. 9, 2008

(30) Foreign Application Priority Data
Apr. 28, 2004    (KR) .................. 10-2004-0029638

(51) Int. Cl.
*C12N 1/20* (2006.01)
(52) U.S. Cl. .................. 435/252.4; 424/93.3

(58) Field of Classification Search ............... None
See application file for complete search history.

(56) References Cited

U.S. PATENT DOCUMENTS

| | | | |
|---|---|---|---|
| 5,342,779 A | 8/1994 | Matsumura et al. | |
| 5,705,072 A | 1/1998 | Haase | |
| 6,383,797 B1 | 5/2002 | Lee | |
| 6,406,882 B1 * | 6/2002 | Kumar et al. | .................. 435/42 |

OTHER PUBLICATIONS

Saagua et al., International Biodeterioration and Biodegradation, vol. 31 (1998,) pp. 39-43.*
Novakova et al., International Biodeterioration & Biodegradation 50 (2002) 47-54.*

* cited by examiner

*Primary Examiner*—Irene Marx
(74) *Attorney, Agent, or Firm*—Gerald E. Hespos; Michael J. Porco

(57) ABSTRACT

Disclosed is a novel bacterial consortium comprise bacterial strains useful for effectively treating endocrine disrupters and a method for treating endocrine disrupters using the same. The invention provides a method for biologically restoring soils, wastes and water, etc. which are polluted with chlorinated compounds such as polychlorinated biphenyl (PCBs), dioxin, pentachlorophenol (PCP), perchloroethylene (PCE), trichloroethylene (TCE) and 1,1,1-trichloroethane (1,1,1-TCA), etc., polycyclic aromatic hydrocarbons (PAH) and petroleum-tar acids, and toluene which are all known as representative endocrine disrupters.

1 Claim, 9 Drawing Sheets

US 7,745,199 B2

BACTERIAL CONSORTIUM NBC2000 AND METHOD FOR BIOLOGICALLY TREATING ENDOCRINE DISRUPTERS USING THE NBC2000

TECHNICAL FIELD

The present invention relates to a novel bacterial consortium useful for treating endocrine disrupters and a method for treating endocrine disrupters using the same. More specifically, the present invention relates to a bioremediation method of soils, wastes and water, etc. which are contaminated with organic-chlorinated compounds such as polychlorinated biphenyl (PCBs), dioxin, pentachlorophenol (PCP), perchloroethylene (PCE), trichloroethylene (TCE), 1,1,1-trichloroethane (1,1,1-TCA), polycyclic aromatic hydrocarbon (PAH) and petroleum-tar acid, and toluene which are all endocrine disrupters.

BACKGROUND ART

Endocrine disrupters that are most serious one of environmental problems in the earth are classified into about 140 categories and mostly comprise chlorine compound and heavy metals. The endocrine disrupters have extensively polluted the atmosphere, water, soils and food chain of mankind for past several centuries together with the Industrial Revolution, the environmental pollution of the earth and the economic developments. Since extremely small quantities of the materials have been continuously accumulated and formless toxicity was maximized through the food chain of an ecosystem, abnormal behaviors of animals and a human being and generation rate of cancers are increased and chaotic states the generative function such as destruction of an immune system and decrease of the number of sperms are accelerated. Particularly, since the endocrine disrupters fatally acts on the generative function, extermination of mankind and invisible dangers of the survival are being increased.

Regarding polychlorinated biphenyl, which is a toxic substance, only a research of a microbial reaction with several congeners thereof in a level of a concentration of 1 mg/kg or less under a condition of an anaerobic experiment was reported. Any research has not been tried in the inside and outside of the country, regarding aerobic conditions, various congeners of PCBs and in situ soils. It was also tried a research regarding chlorinated compounds such as PCE, etc. under an anaerobic condition using microbes, but it was difficult to carry out the experiment in view of costs of equipments and processing efficiency. In addition, heat treatment of incineration, neutralization with chemicals, solidification by a physical high-pressure condensation, washing and reclamation, etc. are tried, but there are many problems of side effects thereof (for example, unbalance of ecosystem and increase of secondary pollution by dioxin, etc.) and costs. A fundamental treatment of dioxin has never been also tried. Toluene and PAH have many biological treatment limits, and even a basic investigation of biological treatments of petroleum-tar acid, which is by-products of the petrochemical industry, is not tried yet.

Mineral oil comprising a large amount of PCBs, for example, insulator mineral oil that had been used as oil of converters for the previous century, became another problem in this century. In fact, such insulator mineral oil comprising a large amount of PCBs is left untreated in a large scale. Therefore, a method for decomposing such mineral oil has been keenly required.

DISCLOSURE OF INVENTION

Accordingly, the present invention has been made to solve the above-mentioned problems occurring in the prior art. The object of the present invention is to find out novel natural useful microbes present in an ecosystem such as soils and water and thus to provide an ecological restoration technique of fundamentally removing endocrine disrupters polluting global environments by an environment-friendly method.

In order to accomplish the objects, there is provided a bacterial consortium NBC 2000 comprising *Pseudomonas* sp. Cy100 strain (hereinafter, referred to as "Cy100"), *Serratia* sp. Aeng18 strain (hereinafter, referred to as "Aeng18"), *Pseudomonas* sp. Djhc strain (hereinafter, referred to as "Djhc"), *Pseudomonas* sp. Ntar3 strain (hereinafter, referred to as "Ntar3"), *Serratia* sp. Ntar2 strain (hereinafter, referred to as "Ntar2"), *Pseudomonas* sp. EBC107 strain (hereinafter, referred to as "EBC107"), *Pseudomonas aeruginosa* Tnh strain (hereinafter, referred to as "Tnh"), *Aeromonas hydrophila* Aeng17 strain (hereinafter, referred to as "Aeng17"), Pseudomonas aeruginosa Pcpts strain (hereinafter, referred to as "Pcpts"), *Stenotrophomonas maltophilia* Ntar1 strain (hereinafter, referred to as "Ntar1"), *Pseudomonas aeruginosa* Sp300 strain (hereinafter, referred to as "Sp300"), *Chryseomonas luteola* Gc501 strain (hereinafter, referred to as "Gc501"), *Chryseomonas* sp. Gc500 strain (hereinafter, referred to as "Gc500"), *Chryseomonas luteola* Gc300 strain (hereinafter, referred to as "Gc300"), *Brevundimonas vesicularis* Cy101 strain (hereinafter, referred to as "Cy101"), *Brevundimonas vesicularis* Cy102 strain (hereinafter, referred to as "Cy102"), *Brevundimonas vesicularis* Cy103 strain (hereinafter, referred to as "Cy103"), *Bacillus stearothermophilus* Bs100 strain (hereinafter, referred to as "Bs100"), *Bacillus stearothermophilus* Cy104 strain (hereinafter, referred to as "Cy104"), *Bacillus* sp. Cy105 strain (hereinafter, referred to as "Cy105"), *Bacillus* sp. Cy106 strain (hereinafter, referred to as "Cy106"), *Bacillus* sp. Cy107 (hereinafter, referred to as "Cy107"), *Bacillus cereus* EBC106 strain (hereinafter, referred to as "EBC106"), Bs101 strain which is petroleum-tar acid decomposition gram-positive bacteria ((hereinafter, referred to as "Bs101"), Nz2001 strain which is sulfur strain (hereinafter, referred to as "Nz2001") and W24 strain which is oil decomposition gram-negative bacteria (hereinafter, referred to as "W24")

According to another embodiment of the invention, there is provided a method for treating endocrine disrupters using the above bacterial consortium NBC2000.

In the method according to the invention, the endocrine disrupters comprise chlorine compounds such as polychlorinated biphenyl (PCBs), dioxin, pentachlorophenol (PCP) and perchloroethylene (PCE), petroleum hydrocarbon and petroleum-tar acid, and toluene.

The method according to the invention may use the bacterial consortium EBC1000 (KCTC 0652 BP) (Korean Patent No. 284313, U.S. Pat. No. 6,383,797, Australian Patent No. 759338, New Zealand patent No. 517647) together with the bacterial consortium NBC2000.

According to another embodiment of the invention, there is provided a bacterial consortium treating polychlorinated biphenyl (PCBs), which is an endocrine disrupter, wherein the bacterial consortium essentially comprises Cy106 and further comprises at least one selected from the group consisting of Cy100, EBC107, Tnh, Cy101, Cy102, Cy103, Cy104, Cy107 and EBC106 strains.

According to another embodiment of the invention, there is provided a bacterial consortium treating dioxin and pentachlorophenol (PCP), which are endocrine disrupters, wherein the bacterial consortium essentially comprises at least one selected from the group consisting of EBC100, EBC101, EBC103 and EBC106 strains and further comprises at least one selected from the group consisting of Aeng18, Djhc, Tnh, Aeng17, Pcpts, Sp300, Gc501, Gc500, Gc300 and Nz2001 strains.

According to another embodiment of the invention, there is provided a bacterial consortium treating chlorinated compounds such as perchloroethylene (PCE), trichloroethylene (TCE) and 1,1,1-trichloroethane (1,1,1-TCA), wherein the bacterial consortium essentially comprises at least one of EBC107 and Tnh and further comprises EBC106.

According to another embodiment of the invention, there is provided a bacterial consortium treating petroleum-tar acid, wherein the bacterial consortium essentially comprises at least one selected from the group consisting of Aeng17, Aeng18 and Tnh strains and further comprises at least one selected from the group consisting of Ntar3, Ntar2, Ntar1, Sp300, Bs100, EBC106, Bs101, W24 and Nz2001 strains.

According to another embodiment of the invention, there is provided a bacterial consortium treating toluene, which is an endocrine disrupter, wherein the bacterial consortium essentially comprises at least one of *Bacillus cereus* EBC106 strain and EBC108 which is gram-positive strain and further comprises at least one selected from the group consisting of Aeng17, Aeng18, Nz2001, EBC107 and W24, which is oil decomposition gram-negative strain.

According to another embodiment of the invention, there is provided a bacterial consortium treating residual dioxin, which is a endocrine disrupter, wherein the bacterial consortium comprises *Pseudomonas* sp. Cy100 strain, *Brevundimonas vesicularis* Cy101 strain, *Brevundimonas vesicularis* Cy102 strain, *Brevundimonas vesicularis* Cy103 strain, *Bacillus stearothermophilus* Cy104 strain, *Bacillus* sp. Cy105 strain, *Bacillus* sp. Cy106 strain and *Bacillus* sp. Cy107 strain.

According to another embodiment of the invention, there is provided a bacterial consortium treating mineral oil containing polychlorinated biphenyl (PCBs), which is a endocrine disrupter, wherein the bacterial consortium essentially comprises *Bacillus* sp. Cy106 strain and further comprises at least one selected from the group consisting of *Pseudomonas* sp. Cy100 strain, *Pseudomonas* sp. EBC107 strain, *Pseudomonas aeruginosa* Tnh strain, *Brevundimonas vesicularis* Cy101 strain, *Brevundimonas vesicularis* Cy102 strain, *Brevundimonas vesicularis* Cy103 strain, *Bacillus stearothermophilus* Cy104 strain, *Bacillus* sp. Cy105 strain, *Bacillus* sp. Cy107 strain, *Bacillus cereus* EBC106 strain, *Aeromonas hydrophila* Aeng17 strain, *Serratia* sp. Aeng18 strain, *Bacillus stearothermophilus* Bs100 strain, Nz2001 strain which is sulfur strain and W24 strain which is oil decomposition gram-negative bacteria.

In the method for treating endocrine disrupters and the bacterial consortium, the petroleum-tar acid comprises TPH (total petroleum hydrocarbons), PAH (polycyclic aromatic hydrocarbon), BTEX (benzene, toluene, ethylbenzene, xylene), benzene, ethylbenzene, toluene, xylene, EOX (extractable organic halogens), POX (purgeable organic halogens), halogenated hydrocarbons, chloro-benzene, chlorophenol, PCBs, cyanide, arsenic, lead, cadmium, mercury and sulfur.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
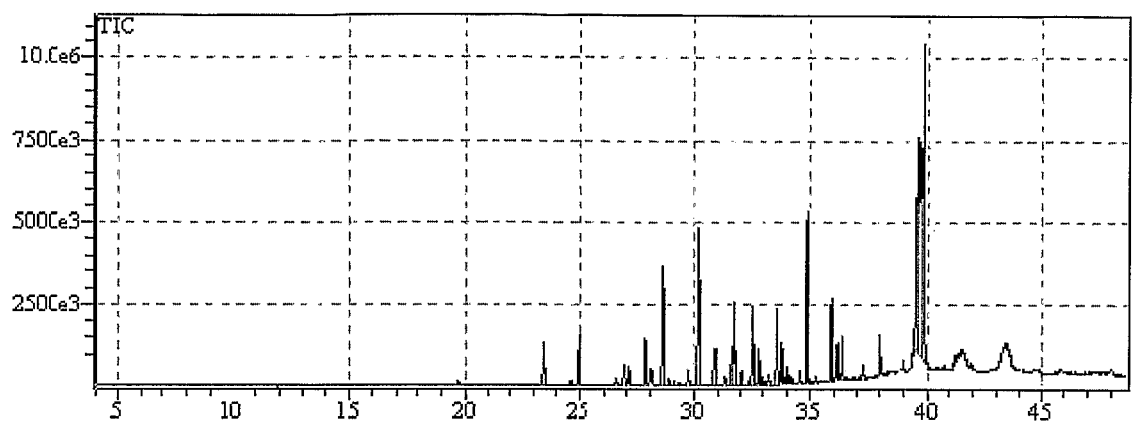
FIG. 1 is a GCMS chromatogram for 97 kinds of standard materials of Aroclor1260.

Hereinafter, preferred embodiments of the present invention will be described with reference to the accompanying drawings. In the following description of the present invention, a detailed description of known functions and configurations incorporated herein will be omitted when it may make the subject matter of the present invention rather unclear.

The invention relates to a novel bacterial consortium NBC2000 which effectively decomposes 209 kinds of congeners of polychlorinated biphenyl in a concentration of 500~1,000 mg/kg soil, 17 kinds of PCDD/PCDF dioxins of 2,500 ng/kg soil, pentachlorophenol (PCP) of 50,000 mg/kg soil, general purpose liquid chlorinated compound (PCE) of 50,000 mg/kg soil, liquid toluene of 40,000 mg/kg, and 100% petroleum-tar acid agglomerate including 20 kinds of toxic substances (for example, TPH (total petroleum hydrocarbons) of 42,600 mg/kg, PAH (polycyclic aromatic hydrocarbon) of 190 mg/kg, BTEX (benzene, toluene, ethylbenzene, xylene) of 3.76 mg/kg, benzene of 0.33 mg/kg, ethylbenzene <0.05 mg/kg, toluene <0.05 mg/kg, xylene of 0.59 mg/kg, EOX (extractable organic halogens) of 76.5 mg/kg, POX (purgeable organic halogens) of 61.8 mg/kg, halogenated hydrocarbons <0.01 mg/kg, chloro-benzene <0.1 mg/kg, chloro-phenol <0.1 mg/kg, PCBs <0.01 mg/kg, cyanide <0.01 mg/kg, arsenic of 0.76 mg/kg, lead of 933 mg/kg, cadmium of 0.14 mg/kg, mercury of 0.66 mg/kg, sulfur of 1.8% and pH 1.2). The petroleum-tar acid has been found in various regions, for example, in soil, ground and seawater environments The inventor isolated NBC2000 (KCTC 10623 BP) from the soils and water, which is a novel strain consortium having characteristics of effectively decomposing the 100% petroleum-tar acid agglomerate wasted in the petrochemical industry complex or a sea area as well as high concentration of organic-chlorinated compounds such as PCBs, dioxin, PCP and PCE and PAH, and toluene contaminated in soils or water.

The bacterial consortium NBC2000 consists of 26 kinds of strains and has an ability of decomposing the toxic substances in a consortium unit according to each combination of the strains. When 209 kinds of congeners of polychlorinated biphenyl contained in the soils were treated with the NBC2000 for 140 days in an aerobic slurry manner, it was found out that almost 100% decomposition was accomplished.

Hereinafter, isolation, identification and activity of a novel strain consortium according to the invention will be described.

1. Isolation of a Novel Bacterial Consortium Capable of Decomposing Endocrine Disrupters.

(1) Isolation of bacteria decomposing PCBs, PCP, dioxin, PCE, toluene and petroleum-tar acid, etc. from soils collected in Korea, South Europe and Oceania, etc.

1 g of collected soil was subject to a shaking culture in Luria-Bertani liquid medium (bacto-tryptone 10 g, bacto-yeast extract 5 g, NaCl 10 g+desalted water 1 liter) for 2~3 days, then 1 ml thereof was taken and each colony was separated in Luria-Bertani agar medium (bacto-tryptone 10 g, bacto-yeast extract 5 g, NaCl 10 g, agar 1.5%+desalted water 950 ml). Each colony separated was selected, sequentially inoculated into a minimal liquid medium ($K_2HPO_4$ 0.065 g, $KH_2PO_4$ 0.017 g, $MgSO_4$ 0.1 g, $NaNO_3$ 0.5 g+desalted water 1 liter) including PCBs, PCP, PCE, toluene and petroleum-tar acid and subject to a shaking culture at 25~30° C. for 3 days or more. While checking the decrease of each toxic substance, 1 ml of the shaking culture solution was taken, sequentially inoculated into Luria-Bertani agar medium and cultured at 25~30° C. for 3~5 days.

Each of purely isolated colonies was again inoculated into the minimal liquid medium and was subject to the shaking culture. Then, about 50 kinds of useful bacteria were separated which had colonies having respective different shape respectively formed individually in Luria-Bertani solid medium and the same colonies occur upon passages culturing thereof.

(2) The above separated bacteria were sequentially inoculated into minimal mediums in which PCBs, PCP, PCE, toluene and petroleum-tar acid were included in stepwise increasing concentrations, respectively. Then, 26 kinds of bacteria surviving at higher concentration were isolated based on strain and the difference of shape by repeating the same method as the above (1).

The obtained 26 kinds of bacteria were composed as a consortium and referred to as NBC2000. Each of the bacteria constituting the bacterial consortium was respectively named as Cy100, Cy101, Cy102, Cy103, Cy104, Cy105, Cy106, Cy107, Ntar1, Ntar2, Ntar3, Gc300, Gc500, Gc501, Bs100, Aeng17, Aeng18, Sp300, Tnh, Djhc, Pcpts, EBC106, EBC107, Bs101, W24 and Nz2001.

The bacterial consortium NBC2000 according to the invention was internationally deposited on Apr. 16, 2004 at Korean Collection for Type Cultures (KCTC) authorized by the World Intellectual Property Organization (WIPO) under the Budapest Treaty, which could be contacted by its address: KCTC in Korea Research Institute of Bioscience and Biotechnology, #52, Oun-dong, Yusong-ku, Taejon 305-333, Republic of Korea, or its internet site: http://kctc.kribb.re.kr/_KTC/SEARCH/M/SearchForm.

2. An Establishment of an Optimum Condition for the Growth of the Bacterial Consortium NBC2000.

When the consortium was subject to a shaking culture in Luria-Bertani nutrient medium (bacto-tryptone 10 g, bacto-yeast extract 5 g, NaCl 10 g/desalted 1 liter), at pH 6~8, 25~30° C. and 80~120 rpm for 48~96 hours, it grew optimally and also grew well in passages culturing under the same conditions.

3. A Biochemical Identification of the Bacterial Consortium NBC2000.

Identification of each of the bacteria purely isolated from the soils was carried out by API20E, API20NE, API50CH and API50CHB, etc. which are API Kits purchased from bioMerieux (bioMerieux sa 69280 Marcy I'Etoile/France) and thus generic names of 23 kinds of bacteria were determined (Table 1 to 4)

TABLE 1

| Test Items | Strains | | | | | |
| --- | --- | --- | --- | --- | --- | --- |
| | Cy100 | Aeng18 | Djhc | Ntar3 | Ntar2 | Ebc107 |
| Ortho-nitro-phenyl-β-D-galactopyranoside | − | + | − | − | + | − |
| Arginin | + | + | + | + | + | + |

TABLE 1-continued

| Test Items | Cy100 | Aeng18 | Djhc | Ntar3 | Ntar2 | Ebc107 |
|---|---|---|---|---|---|---|
| Lysine | − | + | − | − | + | − |
| Ornithine | − | + | − | − | + | − |
| Sodium citrate | + | + | + | + | + | + |
| Sodium thiosulfate | − | − | − | − | − | − |
| Urea | − | − | + | − | − | − |
| Tryptophan | + | + | + | + | + | + |
| Indole | − | − | − | − | − | − |
| Sodium pyruvate | − | + | − | + | + | − |
| Kohn gelatin | − | + | − | − | − | − |
| Glucose | − | − | − | − | + | − |
| Mannitol | − | + | − | − | + | − |
| Inositol | − | + | − | − | + | − |
| Sorbitol | − | + | − | − | + | − |
| Rhamnose | − | − | − | − | − | − |
| Sucrose | − | + | − | − | + | − |
| Melibiose | − | − | − | − | − | − |
| Amygdalin | − | + | − | − | + | − |
| Arabinose | − | − | − | − | − | − |
| Oxidase | + | − | + | + | − | + |
| Reduction of nitrate to nitrite | − | + | − | + | + | − |
| Reduction of nitrate to nitrogen gas | + | − | + | − | − | + |
| Mobility | + | + | + | + | + | + |
| MacConkey medium | + | + | + | + | + | + |
| Sodium Chloride (4%) | + | + | + | + | + | + |
| Gram strain | − | − | − | − | − | − |
| Result of identification | Pseudomonas sp. | Serratia sp. | PseudomonAs sp. | Pseudomonas sp. | Serratia sp. | Pseudomonas sp. |

TABLE 2

| Test Items | Tnh | Aeng17 | Pcpts | Ntar1 | Sp300 |
|---|---|---|---|---|---|
| Potassium nitrate (NO$_3$—NO$_2$) | + | + | − | + | + |
| Tryptophan (Indole) | − | +− | − | − | − |
| Glucose (acidification) | − | + | − | + | − |
| Arginin | − | + | − | + | − |
| Urea | +− | + | + | + | + |
| Escurine | + | + | + | + | + |
| Gelatin | + | + | + | + | + |
| p-nitrophenyl-β-D-galactopyranoside | − | + | − | + | − |
| Glucose (assimilation) | + | + | + | − | + |
| Arabinose | − | − | − | − | − |
| Mannose | − | + | − | + | − |
| Mannitol | + | + | + | − | + |
| N-acetyl glucosamine | + | + | + | + | + |
| Maltose | − | + | − | + | − |
| Gluconate | + | + | + | − | + |
| Caprate | + | + | + | − | + |
| Adipate | − | − | + | − | − |
| Malate | + | + | + | + | + |
| Citrate | + | + | + | + | + |
| Phenyl acetate | − | + | − | − | − |
| Tetramethyl-p-phenylenediamine (oxidase) | + | + | + | − | + |
| Mobility | + | + | + | + | + |
| MacConkey medium | + | + | + | + | + |

TABLE 2-continued

| Test Items | Strains | | | | |
|---|---|---|---|---|---|
| | Tnh | Aeng17 | Pcpts | Ntar1 | Sp300 |
| Sodium Chloride (4%) | + | + | + | + | + |
| Gram strain | − | − | − | − | − |
| result of identification | *Pseudomonas aeruginosa* | *Aeromonas hydrophila* | *Pseudomonas aeruginosa* | *Stenotrophomonas maltophialla* | *Pseudomonas aeruginosa* |

TABLE 3

| Test Items | Strains | | | | | |
|---|---|---|---|---|---|---|
| | Gc501 | Gc500 | Gc300 | Cy101 | Cy102 | Cy103 |
| Potassium nitrate (NO$_3$—NO$_2$) | + | + | + | − | − | − |
| Tryptophan (Indole) | − | − | − | − | − | − |
| Glucose (acidification) | + | − | + | − | − | − |
| Arginin | − | − | + | − | − | − |
| Urea | − | − | + | − | − | − |
| Escurine | + | + | + | + | + | + |
| Gelatin | − | − | − | − | − | − |
| p-nitrophenyl-β-D-galactopyranoside | + | + | + | − | − | − |
| Glucose (assimilation) | + | + | + | − | − | − |
| Arabinose | + | + | + | − | − | − |
| Mannose | + | + | + | − | − | − |
| Mannitol | + | + | + | − | − | − |
| N-acetyl glucosamine | + | + | + | − | − | − |
| Maltose | + | + | + | − | − | − |
| Gluconate | + | + | + | − | − | − |
| Caprate | − | − | − | − | − | − |
| Adipate | − | − | − | − | − | − |
| Malate | + | − | + | − | − | − |
| Citrate | + | + | + | − | − | − |
| Phenyl acetate | + | − | + | − | − | − |
| Tetramethyl-p-phenylenediamine | − | − | − | + | + | + |
| Mobility | + | + | + | + | + | + |
| MacConkey medium | + | + | + | + | − | + |
| Sodium Chloride (4%) | + | + | + | − | + | + |
| Gram strain | − | − | − | − | − | − |
| Result of identification | *Chryseomonas luteola* | *Chryseomonas sp.* | *Chryseomonas luteola* | *Brevundimonas vesicularis* | *Brevundimonas vesicularis* | *Brevundimonas vesicularis* |

TABLE 4

| Test Items | Strains | | | | | |
|---|---|---|---|---|---|---|
| | Bs100 | Cy104 | Cy105 | Cy106 | Cy107 | Ebc106 |
| Control | − | − | − | − | − | − |
| Glycerol | + | − | + | − | − | − |
| Erythritol | − | − | − | − | − | − |
| D-arabinose | − | − | − | − | − | − |
| L-arabinose | − | − | + | − | − | − |
| Ribose | − | − | − | − | − | + |
| D-xylose | − | − | + | − | − | − |
| L-xylose | − | − | − | − | − | − |
| Adonitol | − | − | − | − | − | − |
| β-methyl-D-xylose | − | − | + | − | − | − |
| Galactose | + | − | − | − | − | − |
| D-glucose | + | − | + | − | − | + |
| D-Fructose | + | + | + | − | − | + |
| D-mannose | − | + | + | − | − | + |
| L-sorbose | − | − | − | − | − | − |
| Rhamnose | − | − | − | − | − | − |
| Dulcitol | − | − | − | − | − | − |

TABLE 4-continued

| Test Items | Strains | | | | | |
|---|---|---|---|---|---|---|
| | Bs100 | Cy104 | Cy105 | Cy106 | Cy107 | Ebc106 |
| Inositol | − | − | − | − | − | − |
| Mannitol | − | + | + | − | − | − |
| Sorbitol | − | − | − | − | − | − |
| α-methyl-D-mannoside | − | − | − | − | − | − |
| α-methyl-D-glucoside | − | − | − | − | − | − |
| N-acetyl-glucosamine | + | − | + | − | − | − |
| Amygdalin | − | − | − | − | − | − |
| Arbutin | − | − | − | − | − | + |
| Escurine | + | + | + | + | + | + |
| Salicin | − | − | − | − | − | + |
| Cellobiose | − | + | − | − | − | − |
| Maltose | + | + | + | − | − | + |
| Lactose | + | − | − | − | − | − |
| Melibiose | − | − | + | − | − | − |
| Sucrose | + | + | + | − | − | − |
| Trihalose | + | + | + | − | − | + |
| Inulin | − | − | − | − | − | − |
| Melizitose | − | − | + | − | − | − |
| D-raffinose | − | + | + | − | − | − |
| Starch | − | + | + | − | − | + |
| Glycogen | − | + | + | − | − | + |
| Xylitol | − | − | − | − | − | − |
| Gentiobiose | − | − | − | − | − | − |
| D-tranose | + | − | + | − | − | − |
| D-richrose | − | − | − | − | − | − |
| D-tagatose | − | − | − | − | − | − |
| D-fucose | − | − | − | − | − | − |
| L-fucose | − | − | − | − | − | − |
| D-arabitol | − | − | − | − | − | − |
| L-arabitol | − | − | − | − | − | − |
| Gluconate | − | − | − | − | − | − |
| 2-keto-gluconate | − | − | − | − | − | − |
| 5-keto-gluconate | − | − | − | − | − | − |
| Mobility | + | + | + | + | + | + |
| MacConkey Medium | − | − | − | − | − | − |
| Sodium Chloride (4%) | + | + | + | + | + | + |
| Gram strain | + | + | + | + | + | + |
| Result of identification | Bacillus Stearo-thermophilus | Bacillus Stearo-thErmophilus | Bacillus sp. | Bacillus sp. | Bacillus sp. | Bacillus cereus |

4. Isolation of Constituent Strains of the Bacterial Consortium NBC2000.

1) Strain Isolation and Method Thereof

Each strain was purely isolated from soils of Korea, New Zealand, Sweden and Cyprus, etc. and constituted NBC2000. All strains have a characteristic of mobility and thus can be applied to vast and various soils. A method of isolating individual strain from the bacterial consortium NBC2000 is as follows.

(1) Culturing in Luria-Bertani agar medium (bacto-tryptone 10 g, bacto-yeast extract 5 g, NaCl 10 g, agar 1.5%+ desalted water 950 ml).

Cy100: shows up as yellow amorphous colonies having irregular surfaces after the culture for 48 hours and grows up to a size of 4 mm.

Cy101: shows up as ivory semitransparent convex colonies after a culture for 48 hours and grows up to a size of 2.5 mm.

Cy102: shows up as yellow round colonies after the culture for 48 hours and grows up to a size of 2 mm.

Cy103: shows up as ivory round and flat colonies after the culture for 48 hours and grows up to a size of 4 mm.

Cy104: shows up as ivory semitransparent round colonies after the culture for 48 hours and grows up to a size of 4 mm.

Cy105: shows up as ivory round colonies after the culture for 48 hours and grows up to a size of 2.5 mm.

Cy106: shows up as white lusterless round colonies, which is recessed in a center thereof after the culture for 48 hours and grows up to a size of 1.5 mm.

Cy107: shows up as white lusterless round colonies after the culture for 48 hours and grows up to a size of 1 mm.

Ntar1: shows up as yellow semitransparent lustrous round colonies after a culture for 24 hours and grows up to a size of 1 mm.

Ntar2: shows up as beige and ivory lustrous round colonies after a culture for 24 hours and grows up to a size of 2 mm.

Ntar3: shows up as ivory lustrous round colonies after a culture for 48 hours and grows up to a size of 1.5 mm.

Gc300: shows up as ivory lustrous round and convex colonies after a culture for 24 hours and grows up to a size of 3 mm.

Gc500: shows up as ivory lustrous round and convex colonies after a culture for 24 hours and grows up to a size of 1.5 mm.

Gc501: shows up as ivory lustrous round and convex colonies after a culture for 24 hours and grows up to a size of 2.5 mm.

Bs100: shows up as bright ivory round colonies after a culture for 24 hours and grows up to a size of 2 mm.

Aeng17: shows up as red or ivory round or amorphous colonies after a culture for 24 hours and grows up to a size of 3 mm.

Aeng18: shows up as red or ivory round or amorphous colonies after a culture for 24 hours and grows up to a size of 3 mm.

Sp300: shows up as beige and brown round or amorphous colonies after a culture for 24 hours and grows up to a size of 3 mm.

Tnh: shows up as ivory semitransparent colonies having an irregular surface and a metallic color after a culture for 40 hours and grows up to a size of 4 mm. As time goes by, the color of the medium is changed to an indigo blue color.

Djhc: shows up as ivory lustrous round colonies having a smooth surface, which has a high viscosity after a culture for 24 hours and grows up to a size of 3 mm.

Pcpts: shows up as beige and brown round or amorphous colonies after a culture for 24 hours and grows up to a size of 3 mm.

EBC106: shows up as ivory lusterless flat colonies having an irregular surface after a culture for 24 hours and grows up to a size of 7 mm.

EBC107: shows up as ivory semitransparent amorphous colonies having an irregular surface after a culture for 40 hours and grows up to a size of 4 mm.

Bs101: shows up as yellow and ivory round colonies having a rimmed surface after a culture for 24 hours and grows up to a size of 5 mm. It is gram-positive bacteria and has mobility.

W24: shows up as light yellow lustrous round and convex colonies after a culture for 48 hours and grows up to a size of 1.5 mm. It is gram-negative bacteria and has mobility.

Nz2001: shows up as white lusterless colonies after a culture for 48 hours and grows up to a size of 2.5 mm. When it is subject to a long-time culture, hyphae occur on an edge of the colony. It has mobility.

(2) Colors of colonies after a culture in MacConkey solid medium (MacConkey agar: peptone 17 g, proteose peptone 3 g, lactose 10 g, Bile Salts No. 3 1.5 g, NaCl 5 g, agar 13.5 g, neutral red 0.03 g, crystal violet 0.001 g, desalted water 1 liter, pH 7.3~7.5) for 48 hours.

Cy100: light brown small colony occurs.

Ntar1: transparent and light brown, its surface is irregular.

Ntar2: beige small colony.

Ntar3: transparent brown colony exhibiting light red color.

Gc300: deep pink colony, which is beige on its edge.

Gc500: generally beige and pink colony.

Gc501: deep pink colony, which is beige on its edge.

Aeng17 and Aeng18: deep red colonies.

Sp300: beige colony.

Tnh: dark khaki colony.

Djhc: the center of the colony is light pink and an edge thereof is beige.

Pcpts: light khaki.

EBC107: very light pink colony.

Nz2001: pink and beige colony.

In Cy101, Cy102, Cy103, Cy104, Cy105, Cy106, Cy107, Bs100, EBC106, Bs101 and W24 strains, any colony doesn't occur even after a culture for 48 hours.

(3) Colors of colonies after a culture in desoxycholate solid medium (desoxycholate agar: proteose peptone 10 g, lactose 10 g, desoxycholate sodium 0.5 g, NaCl 5 g, sodium citrate 2 g, agar 15 g, neutral red 0.03 g, desalted water 1 liter, pH 7.3~7.5) for 48 hours.

In Cy101, Cy102, Cy103, Cy104, Cy105, Cy106, Cy107, Bs100, EBC106, Bs101 and W24 strains, any colony doesn't occur even after a culture for 48 hours.

Cy100: yellow colony exhibiting light pink having a wrinkle shape like a flower.

Ntar1, Ntar2 and Ntar3: transparent orange color colony.

Gc300 and Gc501: deep pink colony, which is beige on its edge.

Gc500: beige colony exhibiting light red.

Aeng17 and Aeng18: deep red colony.

Sp300: transparent light brown colony.

Tnh: light brown colony exhibiting metallic color.

Djhc: light pink and beige are mixed.

Pcpts: transparent brown colony.

EBC107: yellow colony.

Nz2001: beige colony exhibiting red.

Since it was difficult to identify Bs101 decomposing petroleum-tar acid, sulfur strain Nz2001 and oil decomposition strain W24 by the current method, they were determined as non-identified strains.

5. Decomposition Range of Each of Endocrine Disrupters by the Individual Strain of the NBC2000.

1) Decomposition Range of Endocrine Disrupters by the Each Separated Strain.

Measurements for PCBs, dioxin, PCE, toluene and petroleum-tar acid were made under the optimum conditions of laboratory using the constituent bacteria of the bacterial consortium. Those for sulfur and PCP were mean values measured in a level of individual strain.

*Pseudomonas* sp. Cy100: PCBs 700 mg/kg;

*Serratia* sp. Aeng18: PCP 500 mg/kg, petroleum-tar acid, dioxin 100 ng/kg;

*Serratia* sp. Ntar2: petroleum-tar acid;

*Pseudomonas* sp. Djhc: PCP 1,000 mg/kg, dioxin 300 ng/kg;

*Pseudomonas* sp. Ntar3: petroleum-tar acid;

*Pseudomonas* sp. EBC107: PCBs 700 mg/kg, PCP 100 mg/kg, dioxin 100 ng/kg, PCE 50,000 mg/kg;

*Pseudomonas* sp. Tnh: PCBs 700 mg/kg, PCP 500 mg/kg, dioxin 300 ng/kg, PCE 50,000 mg/kg, petroleum-tar acid;

*Aeromonas* sp. Aeng17: petroleum-tar acid, PCP 100 mg/kg, dioxin 50 ng/kg;

*Pseudomonas* sp. Pcpts: PCP 1,000 mg/kg, dioxin 500 ng/kg;

*Stenotrophomonas* sp. Ntar1: petroleum-tar acid;

*Pseudomonas* sp. Sp300: petroleum-tar acid, PCP 700 mg/kg, dioxin 100 ng/kg;

*Chryseomonas* sp. Gc501: PCP 500 mg/kg, dioxin 100 ng/kg;

*Chryseomonas* sp. Gc500: PCP 500 mg/kg, dioxin 100 ng/kg;

*Chryseomonas* sp. Gc300: PCP 300 mg/kg, dioxin 100 ng/kg;

*Brevundimonas* sp. Cy101: PCBs 150 mg/kg;

*Brevundimonas* sp. Cy102: PCBs 150 mg/kg;

*Brevundimonas* sp. Cy103: PCBs 700 mg/kg;

*Bacillus* sp. Bs100: petroleum-tar acid;

*Bacillus* sp. Cy104: PCBs 800 mg/kg;

*Bacillus* sp. Cy105: PCBs 700 mg/kg;

*Bacillus* sp. Cy106: PCBs 1,000 mg/kg;

*Bacillus* sp. Cy107: PCBs 150 mg/kg;

*Bacillus* sp. EBC106: PCBs 700 mg/kg, PCP 1,000 mg/kg, dioxin 300 ng/kg, petroleum-tar acid, PCE 50,000 mg/kg, toluene 50,000 mg/kg;

Gram-positive bacteria Bs101: petroleum-tar acid;

Gram-negative bacteria W24: TPH 100 mg/kg, toluene 100 mg/kg;

Sulfur strain Nz2001: sulfur, petroleum-tar acid, dioxin 50 ng/kg.

6. Decomposition Characteristics of Endocrine Disrupters of the Bacterial Consortium NBC2000 and Several Combinations of the Constituent Strains.

A decomposition ability of an individual strain is limited. However, when the whole NBC2000 or bacterial consortiums according to each combination of strains constituting the NBC2000 is treated in a sample or polluted environments, wider and more effective decomposition effect is obtained. This means that a synergy effect due to mutual cooperation as the bacterial consortiums is very high, rather than the functions of the individual strain constituting the NBC2000. Any strain cannot decompose endocrine disrupters such as PCBs, dioxin and petroleum-tar acid, etc. as an individual strain. However, according to combinations of each strain of the NBC2000 and each strain of EBC1000, an effective decomposition effect is provided due to mutual supplementation between the strains and gene transfer-exchange. In order to prove the effect, the inventor carried out the following tests.

Experimental Example 1

A Biodegradation Treatment Experiment on PCBs-Polluted Soils and Insulator Oil

Experimental Condition

1) Biodegradation Experiment on Aroclor 1242, 1254 and 1260 under an Aerobic Condition.

Aroclor 1254 and 1260, which are standard substances of PCBs, were purchased and used from AccuStandard, Inc. (125 Market st. New haven, Conn. 06513) as an article in which they were dissolved in hexane in a concentration of 1.0 mg/ml. Aroclor 1254 consists of 112 congeners and Aroclor 1260 consists of 97 congeners. They are used as standard substances for verification of PCBs.

Each of strains constituting the NBC2000 and each of strains constituting the EBC1000 were combined to verify the decomposition of Aroclor 1254 and 1260 PCBs. Specifically, the PCBs treatment abilities of Tnh alone (Comparative examples 1 and 2), a bacterial consortium consisting of Tnh and EBC strains (Example 1 and 4), a bacterial consortium consisting of Cy100, Cy103, Cy104, Cy105, Cy106 and Cy107 (Example 2 and 5) and a bacterial consortium consisting of Tnh, EBC1000, Cy100, Cy103, Cy104, Cy105, Cy106 and Cy107 (Examples 3 and 6) were verified. For this purpose, an undiluted solution of Aroclor 1254 was added in an amount of 10% to 10 ml of a minimal medium (pH 7.2) which was made by dissolving 0.065 g $K_2HPO_4$, 0.017 g $KH_2PO_4$, 0.1 g $MgSO_4$, 0.5 g $NaNO_3$ in 1 liter of desalted water. The each of the bacterial consortiums was inoculated into the mixture in an amount of $10^5 \sim 10^6$/ml and then was subject to a shaking culture at 30° C. and 150 rpm under an aerobic state (Table 5). Aroclor 1260 was also similarly prepared to 1254. The results were shown in Tables 5 and 6.

TABLE 5

| Treatment period/days | Comparative example 1 (Tnh) | | Example 1 (Tnh + EBC106 + EBC107) | | Example 2 (Cy100 + Cy101 + Cy102 + Cy103 + Cy104 + Cy105 + Cy106 + Cy107) | | Example 3 (Tnh + EBC106 + EBC107 + Cy100 + Cy101 + Cy102 + Cy103 + Cy104 + Cy105 + Cy106 + Cy107) | |
|---|---|---|---|---|---|---|---|---|
| | Aroclor 1254 (mg/ml) | Number of Microbe (cfu/ml) | Aroclor 1254 (mg/ml) | Number of Microbe (cfu/ml) | Aroclor 1254 (mg/ml) | Number of Microbe (cfu/ml) | Aroclor 1254 (mg/ml) | Number of Microbe (cfu/ml) |
| 0 | 0.1 | $7.2 \times 10^5$ | 0.1 | $7.0 \times 10^5$ | 0.1 | $4.4 \times 10^5$ | 0.1 | $6.8 \times 10^5$ |
| 12 | 0.1 | ND* | ND | $8.0 \times 10^7$ (Tnh) | ND | $2.2 \times 10^8$ (Cy106) | ND | $7.4 \times 10^7$ (Cy106, Tnh) |

*ND: not detected

As can be seen from the result of the experiments, Tnh strain alone could not decompose Aroclor 1254 PCBs at all. However, when combined with EBC strains, the Tnh strain was increased by 100 times or more, and thus PCBs were mostly decomposed. In addition, when only the Cy strains were combined, the Cy106 strain was increased by about 1,000 times and thus all PCBs were decomposed. Additionally, when the Tnh, EBC and Cy strains were combined, Tnh and Cy106 were increased by 100 times or more, respectively, and thus the PCBs were mostly decomposed. In the Table 5, the strain in parentheses next to the number of microbe indicates dominant species. The increase of microbes means that the microbes were proliferated using the PCBs as nutrient sources. On the contrary, the decrease of microbe's means that multi-functional genes decomposing the PCBs were lost or not obtained in the combinations of microbes and thus the microbes were restrained from growing or annihilated due to the PCBs which are toxic pollutants.

Accordingly, it can be understood that it is difficult to treat the Aroclor 1254 consisting of 112 kinds of congeners among 209 kinds of congeners with the individual strain only and it can be treated by a mutual interaction between various kinds of strains having decomposition ability, which can be applied to the actual sample or field-test.

TABLE 6

| | Treatment period (days) | Aroclor 1260 (mg/ml) | Insulator mineral oil containing Aroclor 1254; Aroclor 1254 (mg/ml)/ insulator mineral oil (ml) | Insulator mineral oil containing Aroclor 1242; Aroclor 1242 (mg/ml)/ insulator mineral oil (ml) | Number of microbes (cfu/ml) |
|---|---|---|---|---|---|
| Comparative example 2 (Tnh) | 0 | 0.1 | | | $3.2 \times 10^5$ |
| | 30 | 0.1 | | | ND* |
| Comparative example 3 (Cy106) | 0 | 0.1 | | | $2.0 \times 10^7$ |
| | 30 | 0.01 | | | $1.0 \times 10^8$ |
| Comparative example 4 (Tnh + EBC106 + EBC107) | 0 | 0.1 | | | $1.7 \times 10^6$ |
| | 30 | 0.1 | | | $1.0 \times 10^3$ |
| Example 5 (Cy106 + Cy103) | 0 | 0.1 | | | $1.7 \times 10^6$ |
| | 30 | 0.001 | | | $1.5 \times 10^8$ (Cy106) |
| Example 6 (Cy100 + Cy101 + Cy102 + Cy103 + Cy104 + Cy105 + Cy106 + Cy107) | 0 | 0.1 | | | $8.0 \times 10^4$ |
| | 30 | ND | | | $6.2 \times 10^7$ (Cy104, Cy106) |
| Example 7-A (Tnh + EBC106 + EBC107 + Cy100 + Cy101 + Cy102 + Cy103 + Cy104 + Cy105 + Cy106 + Cy107) | 0 | 0.1 | | | $7.6 \times 10^4$ |
| | 30 | ND | | | $2.4 \times 10^8$ (Cy106) |
| Example 7-B (Tnh + W24 + Aeng17 + Aeng18 + Nz2001 + EBC106 + Cy104 + Cy105 + Cy106 + Cy107 + Bs100) | 0 | | 0.1 & 25 | 0.1 & 25 | $8.8 \times 10^8$ |
| | 30 | | ND & ND | ND & ND | $1.2 \times 10^{11}$ (Cy 106) |

ND: not detected

In the above experiments, Tnh strain alone (Comparative example 2) could not decompose Aroclor 1260 PCBs at all. However, the individual Cy106 (Comparative example 3) strain decomposed a part of Aroclor 1260 PCBs. Even when combined with EBC strains (Comparative example 4), the inoculated strains were decreased by about one thousand times and thus could hardly decompose the PCBs. That is, it can be seen that the microbes were restrained from growing or annihilated due to the toxic PCBs. This means that other strains besides Tnh and EBC strains are required for mutually interacting to decompose PCBs. When the Cy106 was combined with the Cy103 (Example 5), the strains were increased by about 100 times and thus the PCBs were satisfactorily decomposed. When the Cy106 was combined with other Cy strains (Example 6), the Cy104 and Cy106 strains were increased by about 1,000 times, respectively, and all the PCBs were decomposed. When Tnh, EBC and Cy strains were combined (Example 7-A and 7-B), the Cy106 strain was increased by 1,000~10,000 times and thus all PCBs and mineral oil were decomposed. Common dominant species was the Cy106. Accordingly, it can be understood that the Cy106 is required to decompose the PCBs and other strains constituting the NBC2000 should be added to easily decompose most of the PCBs.

The above results mean that it is difficult to perfectly treat the Aroclor 1260, 1254 and 1242 consisting of 97, 112 and 104 kinds of congeners, respectively among 209 kinds of congeners with the individual strain solely and it can be treated by a mutual interaction between various kinds of strains having decomposition ability, which can be applied to the actual sample or field-test.

2) Cyprus Soil 3 kg+Strains+the Condition of Aerobic Slurry State

It was carried out experiments on PCBs biodegradation for actual Cyprus' soil, which was polluted with 97 kinds of PCBs, which are Aroclor 1260 series. 3 kg of Cyprus soil which were polluted with PCBs in a concentration of about 700~1,000 ppm (mg/kg) was repeatedly tested in a unit of 30~60 g under an aerobic slurry condition for a long time. A minimal liquid medium (made by dissolving 0.065 g $K_2HPO_4$, 0.017 g $KH_2PO_4$, 0.1 g $MgSO_4$ and 0.5 g $NaNO_3$ in 1 liter of desalted water; pH 7.2) of 45~90 ml was added to the 30~60 g of Cyprus soil and maintained to be a humidity of 60~80%. Representative experimental examples were carried out with the divided Comparative example 5 and Example 8 as shown in Table 7. In Example 8, the strains constituting the NBC2000 were added and then shaken in an aerobic slurry state at 25° C. and 100 rpm for 138 days. On 38 days, $NO_3N$:$PO_4P$ (=3:1) were added to increase the activity of the strains. As a result of that, when treating with the single strain solely, the PCBs were little decomposed. However, when treating with the combination of two or more strains, the PCBs were satisfactorily decomposed and when treating with various combinations of the strains, the decomposition efficiency was very high. The representative results were shown in Table 7.

TABLE 7

| Treatment period (days) | Comparative example 5 (30 g) | | Example 8 (Tnh + EBC106 + Cy100 + Cy101 + Cy102 + Cy103 + Cy104 + Cy105 + Cy106 + Cy107) (30 g) | |
|---|---|---|---|---|
| | PCBs (mg/kg) | Number of indigenous microbes (cfu/ml) | PCBs (mg/kg) | Number of inoculated microbes (cfu/ml) |
| 0 | 700~1000 | $2.0 \times 10^6$ | 700~1000 | EBC106: $9.0 \times 10^4$, Cy103: $3.6 \times 10^7$ Cy100: $6.0 \times 10^6$, the others.: $2.0 \times 10^8$ |
| 65 | 700~1000 | $2.4 \times 10^6$ | 200~300 | EBC106: $1.0 \times 10^7$, Cy103: $2.0 \times 10^8$ Cy100: $3.0 \times 10^6$, the others: ND* |
| 85 | 700~1000 | $1.0 \times 10^6$ | 100~200 | EBC106: $5.0 \times 10^6$, Cy103: $4.2 \times 10^7$ Cy100: $4.0 \times 10^6$, the others: ND |
| 138 | 700~1000 | $1.0 \times 10^6$ | ND | EBC106: $2.0 \times 10^7$, the others: ND |

*ND: not detected

According to the experiments as described above, in the soil of Comparative example 5 to which the NBC2000 strains were no inoculated, the PCBs were little decomposed even if the soils were shaken to the slurry state and the indigenous strains were also remained to be unchanged. On the contrary, in the soil of Example 8 to which the strains constituting the NBC2000 were inoculated, all PCBs were biodegraded around 138 days. When the NBC2000 strains checked in verifying the Aroclor 1260 were inoculated, EBC106 strain was increased by about 1,000 times and the Cy103 strain was increased by about 10 times on about 65 days, but other strains were remained to be same or not detected. On 85 days, similar phenomena occurred, as on the 65 days though the levels were lower. On 138 days, the EBC106 strain only was increased by about 1,000 times, so that the mutual interactions among the strains and the characteristics of NBC2000 in Cyprus soil ecosystem could be seen. The EBC106 strain mutually interacted with the Tnh and other Cy strains in a manner of conjugation and complementation, thereby exhibiting excellent effects of decomposing the PCBs. However, the individual EBC106 strain alone could little decompose the PCBs. These results were again clearly verified in GCMS data shown in FIGS. 1 to 5.

Figure 2:
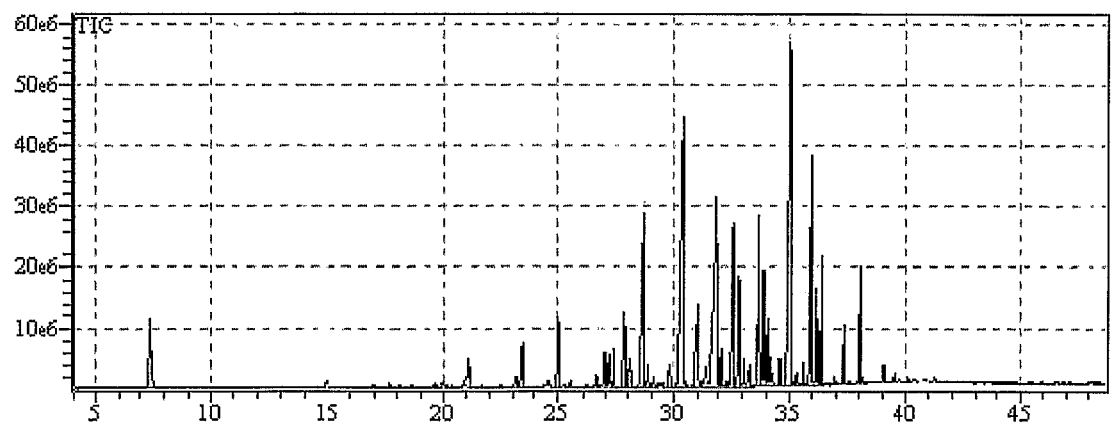
FIG. 2 is a GCMS chromatogram for polychlorinated biphenyl of soil before treating with microbes according to an embodiment of the invention.

FIG. 1 is a GCMS analysis result for 97 kinds of standard substances of Aroclor 1260 in which the PCBs were detected. FIG. 2 shows PCBs analysis provided when the Cyprus soil was analyzed before treating with the microbes in Example 8, which is very similar to FIG. 1.

Figure 3:
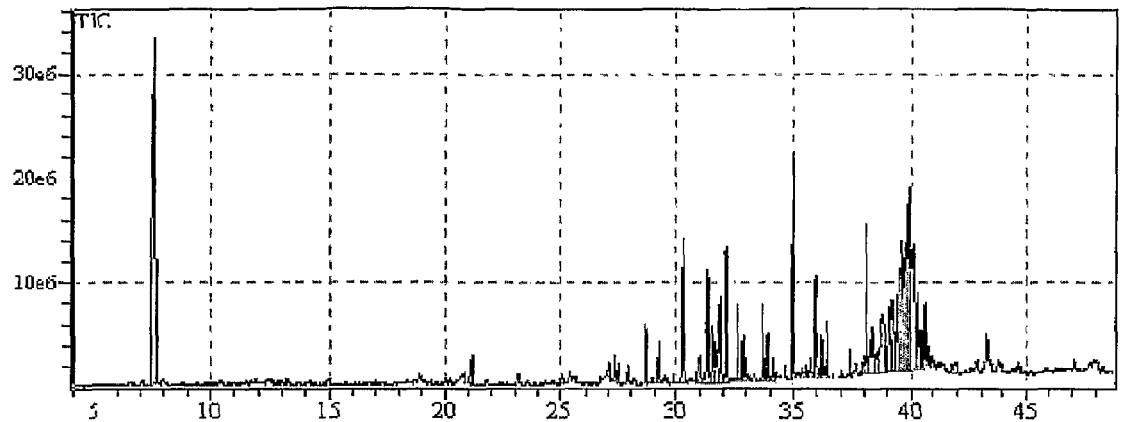
FIG. 3 is a GCMS chromatogram showing that polychlorinated biphenyl was reduced by 50% when it was treated with microbes according to an embodiment of the invention for 65 days.
Figure 4:
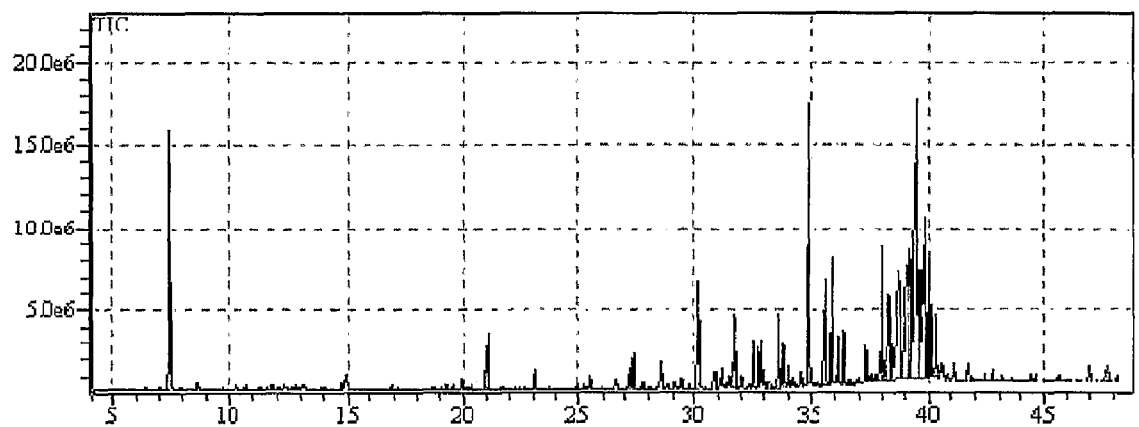
FIG. 4 is a GCMS chromatogram showing that polychlorinated biphenyl was reduced by 80% when it was treated with microbes according to an embodiment of the invention for 85 days.
Figure 5:
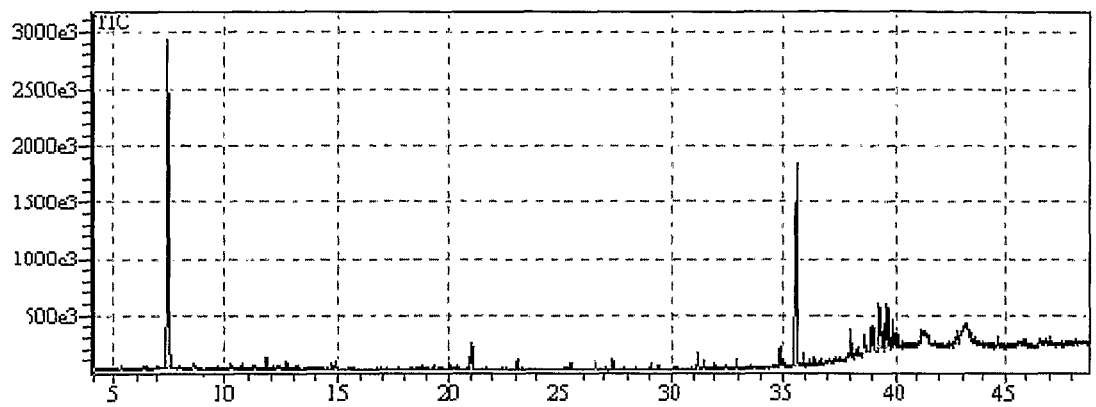
FIG. 5 is a GCMS chromatogram showing that polychlorinated biphenyl was reduced by about 100% when it was treated with microbes according to an embodiment of the invention for 138 days.
Figure 6:
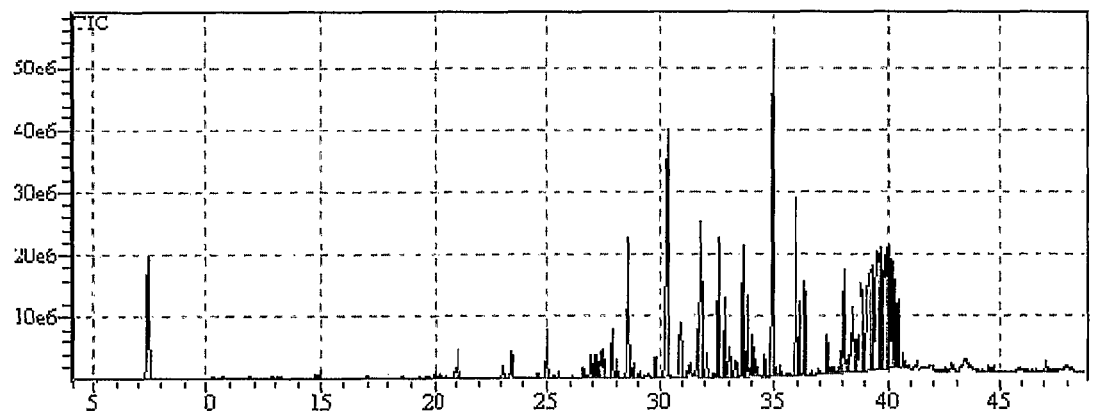
FIG. 6 is a GCMS chromatogram for a control group not treated with microbes according to an embodiment of the invention, wherein 138 days have passed.

FIG. 3 shows that the PCBs were reduced by 50% when treating for 65 days with the consortium of Example 8. The measurement of the amount of reduction was carried out by an area calculating method (Standard Methods and Chemosphere 43(2001) 455-459). FIG. 4 shows that the PCBs were reduced by about 80% when treating for 85 days with the consortium of Example 8, according to the area calculating method. FIG. 5 is a GCMS chromatogram showing that most of the PCBs were decomposed when treating for 138 days with the consortium Example 8 and any congener of the PCBs was not detected. FIG. 6 is a GCMS chromatogram of Comparative example 5 when treating for 138 days, which is nearly similar to the initial shape before treating in Example 8 (FIG. 2). Like this, the GCMS analyses also show that congeners of high concentration of the PCBs having polluted the Cyprus soil were totally biodegraded by the microbes such as the NBC2000.

Experimental Example 2

Biodegradation Treatment of Soils and Timber Polluted with Pentachlorophenol (PCP) and Dioxin GC Analysis (GC2010, Gas Chromatograph, Shimadzu)

1) Swedish Soil 100 g+Strains+$H_2O_2$+Aerobic Slurry Condition

Figure 7:
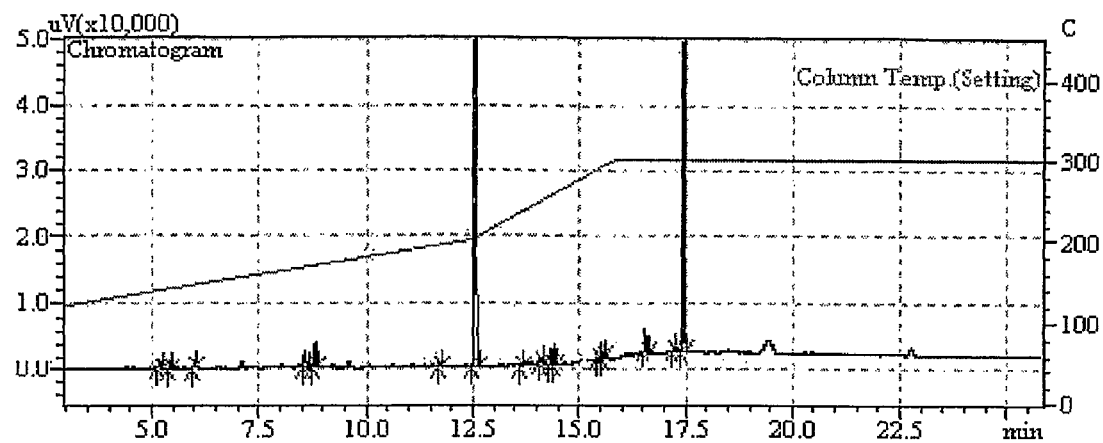
FIG. 7 is a GC chromatogram showing an initial concentration of PCP just before treating with microbes according to an embodiment of the invention.
Figure 8:
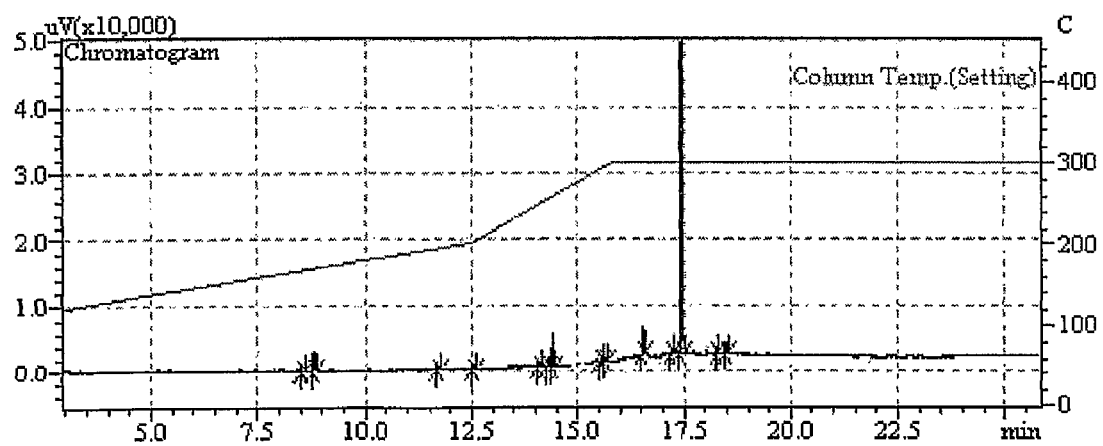
FIG. 8 is a GC chromatogram showing a concentration of PCP after treating with microbes according to an embodiment of the invention for 200 days.

The actual Swedish soil was classified into Comparative example 6 (control group) and Example 9 (test group) in an amount of 100 g, respectively, and the verification thereof was carried out in an aerobic state while shaking at 25~30° C. and 90 rpm. In Comparative example 6, the shaking was carried out using the soil (pH 4.2) and desalted water. In the experimental group, the pH was adjusted to be 7.0, then the minimal liquid medium (0.65 g $K_2HPO_4$, 0.17 g $KH_2PO_4$, 0.5 g $NaNO_3$, 0.1 g $MgSO_4 \cdot 7H_2O$/1 liter desalted water) 200 ml was added and aerobically shaken. The strain which was initially inoculated to the experimental group was EBC1000 slurry of $10^7$/ml slurry, nitrogen ($NO_3$—N) and phosphorus ($PO_4$—P) were added in a ratio of 3:1 around 60 days and 80 days, and 3 ml of $H_2O_2$ was added to promote the biodegradation on 90 days. On 170 days, Sp300, Gc300, Gc500, Gc501, Tnh, Aeng17, Aeng18, Pcpts strains among the NBC2000 strains were additionally inoculated as $10^5$/ml of slurry, the EBC1000 strain was also additionally inoculated as $10^6$/ml of slurry, thereby promoting the decomposition ability. As a result of that, the EBC1000 strains and the NBC2000 strains complementarily acted each other, thereby accelerating the biodegradation. Any strain could not alone decompose the PCP and dioxin in the soil and the consortiums combined with at least two strains satisfactorily decomposed the PCP and dioxin. More specific results were shown in Tables 8 and 9 and FIGS. 7 and 8. Table 8 is a result for PCP, Table 9 is a result for 17 kinds of PCDD/PCDF dioxin. Also, FIG. 7 is a GC chromatograph of an initial PCP concentration in Example 9, and FIG. 8 is a GC chromatograph of the PCP concentration after treating for 200 days in Example 9.

TABLE 8

| Treatment period (days) | Soil of Comparative example 6 (100 g) | | Soil of Example 9 (100 g): EBC100, EBC101, EBC103, EBC106, EBC107, Sp300, Gc300, Gc500, Gc501, Tnh, Aeng17, Aeng18, Pcpts | |
|---|---|---|---|---|
| | PCP (mg/kg) | Number of indigenous Microbes (cfu/ml slurry) | PCP (mg/kg) | Number of inoculated Microbes (cfu/ml slurry) |
| 0 | 50,000 | $2.0 \times 10^5$ | 50,000 | $2.6 \times 10^5$ (EBC100, EBC101, EBC103) the others $10^6$ |
| 21 | | $2.0 \times 10^6$ | | $2.6 \times 10^7$ (EBC100, EBC101, EBC103) |
| 40 | | $4.8 \times 10^6$ | 8,000 | $1.6 \times 10^5$ |
| 170 | | $3.0 \times 10^3$ | | $5.0 \times 10^6$ |
| 200 | 30,000~50,000 | $3.0 \times 10^3$ | 3.6 | $1.6 \times 10^5$ |

As can be seen from the Table 8, in Comparative example 6, the PCP was little changed, but in Example 9, the PCP was reduced by 99.9999%. Also, in GC analyses in FIGS. 7 and 8, the PCP at 12.5 minutes (retention time) was significantly changed on the chromatogram according to whether the microbes of the invention were inputted or not. This is an exact proof of microbe decomposition for the PCP in the Swedish soil. According to the Table 8, the high concentration of PCP was mostly removed due to the strains constituting the EBC1000 and NBC2000 and nitrogen, phosphorous and $H_2O_2$ aiding the activities thereof.

Meanwhile, as shown in Table 9-A, 17 kinds of dioxins which are the most toxic PCDD/PCDF series among the 210 kinds of dioxin congeners were removed by a high ratio, on the average. This analysis was carried out in Analytica AB in Germany (Nytorpsnagen 16, 183 25 Taby.). The results were shown in Table 9-A.

TABLE 9-A

| Sum PCDD/PCDF I-TEQ* | Concentration before treating with the strain (ng/kg dw) 2493.2 | Concentration after treating with the strain (ng/kg dw) 85.83 |
|---|---|---|
| 2,3,7,8-TetraCDD | 18 | ND** |
| 1,2,3,7,8-PentaCDD | 170 | ND |
| 1,2,3,4,7,8-HexaCDD | 47 | 0.89 |
| 1,2,3,6,7,8-HexaCDD | 780 | 11 |
| 1,2,3,7,8,9-HexaCDD | 78 | 1.6 |
| 1,2,3,4,6,7,8-HeptaCDD | 590 | 49 |
| OctaCDD | 58 | 13 |
| 2,3,7,8-TetraCDF | 4.4 | ND |
| 1,2,3,7,8-PentaCDF | 2.7 | ND |
| 2,3,4,7,8-PentaCDF | 75 | 0.9 |
| 1,2,3,4,7,8-HexaCDF | 190 | 1.8 |
| 1,2,3,6,7,8-HexaCDF | 54 | 0.43 |
| 1,2,3,7,8,9-HexaCDF | 7.3 | ND |
| 2,3,4,6,7,8-HexaCDF | 110 | 1.3 |
| 1,2,3,4,6,7,8-HeptaCDF | 250 | 5.1 |
| 1,2,3,4,7,8,9-HeptaCDF | 49 | 0.64 |
| OctaCDF | 9.8 | 0.17 |

**ND: not-detected
I-TEQ* indicates an equivalent factor of dioxins, based on 2,3,7,8-TetraCDD (2,3,7,8-Tetrachloro-dibenzodioxin) in which chlorine atoms are substituted at 2,3,7,8 positions and which is the most toxic dioxin of 17 kinds of toxic dioxins. The concentration of each congener is proliferated by the factor and thus converted to 2,3,7,8-TetraCDD concentrations, wherein the conversion factor is referred to as TCDD toxic equivalent factor. International TEF (I-TEQ) by a joint research of NATO nations is most used and the converted concentration is referred to as TCDD equivalent (TEQ).
TEQ = Σ (TEF X 2,3,7,8-concentraions of substitution isomers).

As shown in Table 9-A, it can be seen that decomposition effects for the 17 kinds of dioxins were very excellent.

The strains, which decomposed dioxin in the above-mentioned experiment, however, could not grow any more due to the existence of the condensed residual dioxin. This implies that at least a part of the residual dioxin congeners are rather more toxic than the crude dioxin congeners mixture. This inventor also designed a bacterial consortium being able to decompose such toxic residual dioxin. The bacterial consortium comprises *Pseudomonas* sp. Cy100 strain, *Brevundimonas vesicularis* Cy101 strain, *Brevundimonas vesicularis* Cy102 strain, *Brevundimonas vesicularis* Cy103 strain, *Bacillus stearothermophilus* Cy104 strain, *Bacillus* sp. Cy105 strain, *Bacillus* sp. Cy106 strain and *Bacillus* sp. Cy107 strain.

In order to demonstrate the effect of the above-mentioned bacterial consortium on the decomposition of such residual dioxin, this inventor carried out the following experiment.

The residual dioxin congeners in the right side of the Table 9-A were treated with $10^5$ cfu/ml of the bacterial consortium comprising Cy100~Cy107 strains related to PCBs biodegradation. The Cy strains are increased to $10^7$ cfu/ml for approximately two month. This demonstrates that the bacteria consortium comprising Cy strains can adapt to such toxic condition of condensed residual dioxin very well and decompose the residual dioxin, and accordingly grow.

As shown in the following Table 9-B, the 100-fold increase of Cy strains shows that almost all residual dioxin congeners were degraded biologically.

TABLE 9-B

| Sum PCDD/PCDF I-TEQ* | Concentration before treating with the strain (ng/kg dw) 2493.2 | Concentration after treating with the strain (ng/kg dw) 85.83 | Result after addition of Cy100~107 |
|---|---|---|---|
| 2,3,7,8-TetraCDD | 18 | ND** | |
| 1,2,3,7,8-PentaCDD | 170 | ND | |
| 1,2,3,4,7,8-HexaCDD | 47 | 0.89 | Cy strains |
| 1,2,3,6,7,8-HexaCDD | 780 | 11 | increased |
| 1,2,3,7,8,9-HexaCDD | 78 | 1.6 | to 100-fold |
| 1,2,3,4,6,7,8-HeptaCDD | 590 | 49 | |
| OctaCDD | 58 | 13 | |
| 2,3,7,8-TetraCDF | 4.4 | ND | |
| 1,2,3,7,8-PentaCDF | 2.7 | ND | |
| 2,3,4,7,8-PentaCDF | 75 | 0.9 | Cy strains |
| 1,2,3,4,7,8-HexaCDF | 190 | 1.8 | increased |
| 1,2,3,6,7,8-HexaCDF | 54 | 0.43 | to 100-fold |
| 1,2,3,7,8,9-HexaCDF | 7.3 | ND | |
| 2,3,4,6,7,8-HexaCDF | 110 | 1.3 | Cy strains |

TABLE 9-B-continued

| Sum PCDD/PCDF I-TEQ* | Concentration before treating with the strain (ng/kg dw) 2493.2 | Concentration after treating with the strain (ng/kg dw) 85.83 | Result after addition of Cy100~107 |
|---|---|---|---|
| 1,2,3,4,6,7,8-HeptaCDF | 250 | 5.1 | increased to 100-fold |
| 1,2,3,4,7,8,9-HeptaCDF | 49 | 0.64 | |
| OctaCDF | 9.8 | 0.17 | |

**ND: not-detected

2) New Zealand Soil
Strain+Minimal Medium+Desalted Water+$H_2O_2$

The actual New Zealand soil was classified into Comparative example 7 (control group) and Example 10 (experimental group) in an amount of 30 g, respectively, and the verification thereof was carried out in an aerobic state while shaking at 30° C. and 150 rpm. In Comparative example 7, the shaking was carried out using the soil (pH 8.3) and desalted water. In the Example 10, the pH was adjusted to be 8.5, and then 50 ml of the minimal liquid medium (0.65 g $K_2HPO_4$, 0.17 g $KH_2PO_4$, 0.5 g $NaNO_3$, 0.1 g $MgSO_4.7H_2O$/1 liter desalted water) was added and aerobically shaken. In the strain which was initially inoculated to the experimental group, the EBC strain was used as $10^7$/ml slurry, PCP, nitrogen ($NO_3$—N) and phosphorus ($PO_4$—P) were added in a ratio of 100:3:1 around 17, 27 and 50 days and $H_2O_2$ 3 ml was added to promote the biodegradation on 45 days. On 25 and 46 days, Tnh, Pcpts, Sp300, Aeng17, Aeng18 and Nz2001 strains among the NBC2000 strains were additionally inoculated as $10^6$/ml slurry, the EBC strain was also additionally inoculated as $10^7$/ml slurry, thereby promoting the decomposition ability. As a result of that, while little degradation was detected in the case of inoculating individual strains solely, satisfactory degradation efficiency was shown in the case of inoculating combination of two or more strains and very excellent degradation efficiency was shown when more strains were combined. Representative examples thereof were shown in Table 9 and FIGS. 9 and 10.

TABLE 10

| | Soil of Comparative example 7 (30 g) | | Soil of Example 10 (30 g): EBC100, EBC101, EBC103, EBC106, EBC107 + (Tnh, Pcpts, Sp300, Aeng17, Aeng18, Nz2001) | |
|---|---|---|---|---|
| Treatment period (days) | PCP (mg/kg) | Number of Indigenous microbes (cfu/g soil) | PCP (mg/kg) | Number of inoculated microbes (cfu/g soil) |
| 0 | 2500 | $1.0 \times 10^3$ | 2500 | $3.6 \times 10^4$ (EBC106, the others $10^6$) |
| 27 | | $1.2 \times 10^3$ | 540 | $3.0 \times 10^2$ (EBC106), the others. $10^4$ |
| 50 | | $1.4 \times 10^3$ | 106 | $3.0 \times 10^3$ (EBC106), the others $10^4$ |
| 70 | 2300 | $2.0 \times 10^3$ | 26 | $6.0 \times 10^5$ (EBC106) |

As shown in Table 10, the PCP of Comparative example 7 was little changed, but in the Example 10, 99.99% of PCP was reduced. The high concentration of PCP was mostly removed due to the strains constituting the EBC and NBC2000 and catalyst function of nitrogen, phosphorous and $H_2O_2$ aiding the activities thereof.

In the course of general decreases of strains and decomposing the PCP, the EBC106 strain showed that the initially inoculated strains were decreased by 100 times in the course of adaptation and increased by about 1,000 times on 70 days, and continued to show up as dominant species ($10^5$ cfu/g). That is, the EBC106 dominantly played a role in a mutual interaction of microbial combination.

Figure 9:
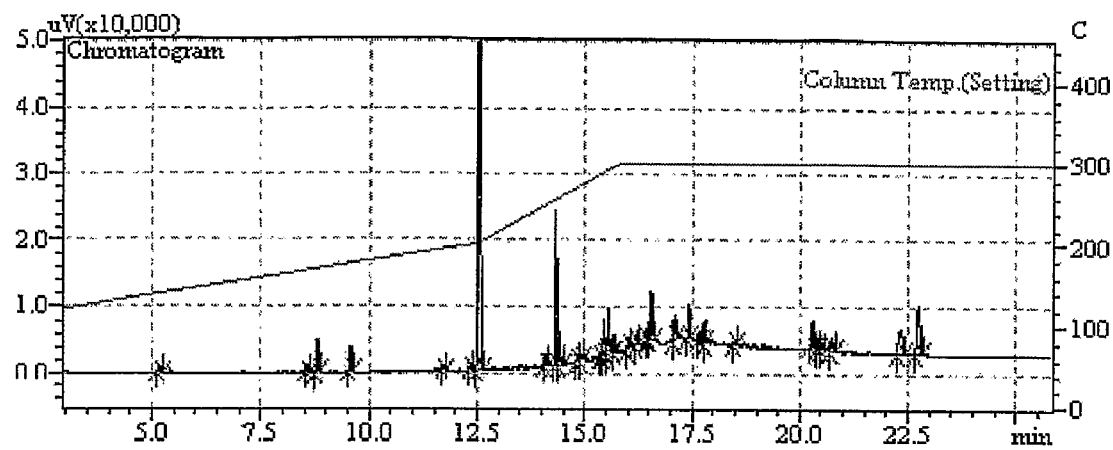
FIG. 9 is a GC chromatogram showing an initial concentration of PCP just before treating with microbes according to an embodiment of the invention.
Figure 10:
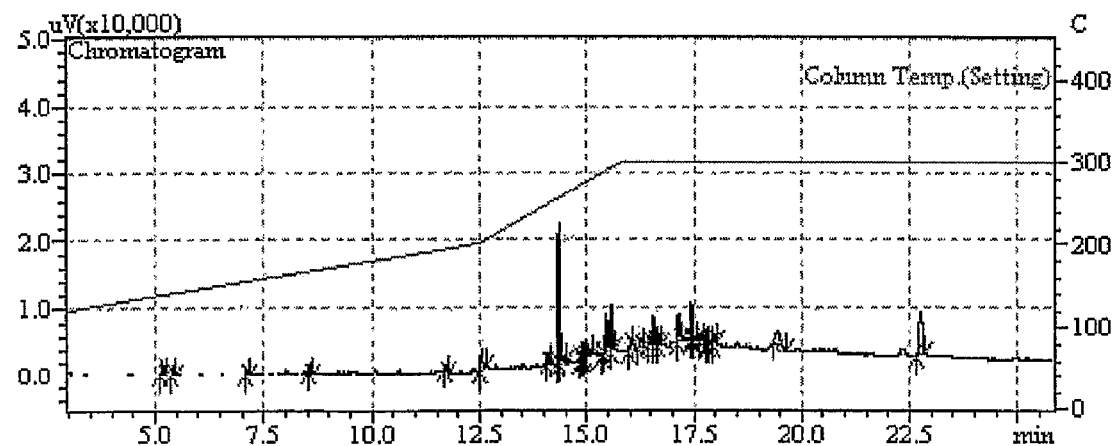
FIG. 10 is a GC chromatogram showing a concentration of PCP after treating with microbes according to an embodiment of the invention, for 70 days.

In addition, the GC analyses in FIGS. 9 and 10 show that the PCP was significantly changed at 12.5 minutes, the initial chromatogram (FIG. 9) didn't appear at all on 70 days. That is, it was again confirmed that in the New Zealand soil, most of PCP was biodegraded by mutual interaction of the microbial flora resulting from fusion of strains constituting the EBC1000 and NBC2000.

3) Plant Treatment of 5 Tons of Ammunition Boxes of the Korean Department of Defense and the Eighth U.S. Army (Example 11).

Figure 11:
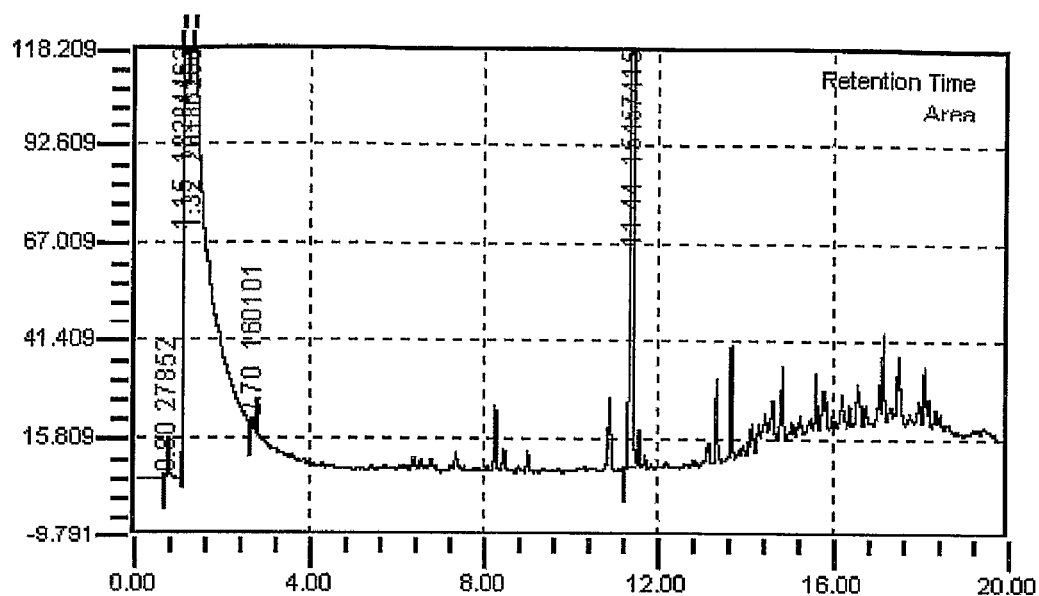
FIG. 11 is a GC chromatogram showing an initial concentration of PCP just before treating with microbes according to an embodiment of the invention.
Figure 12:
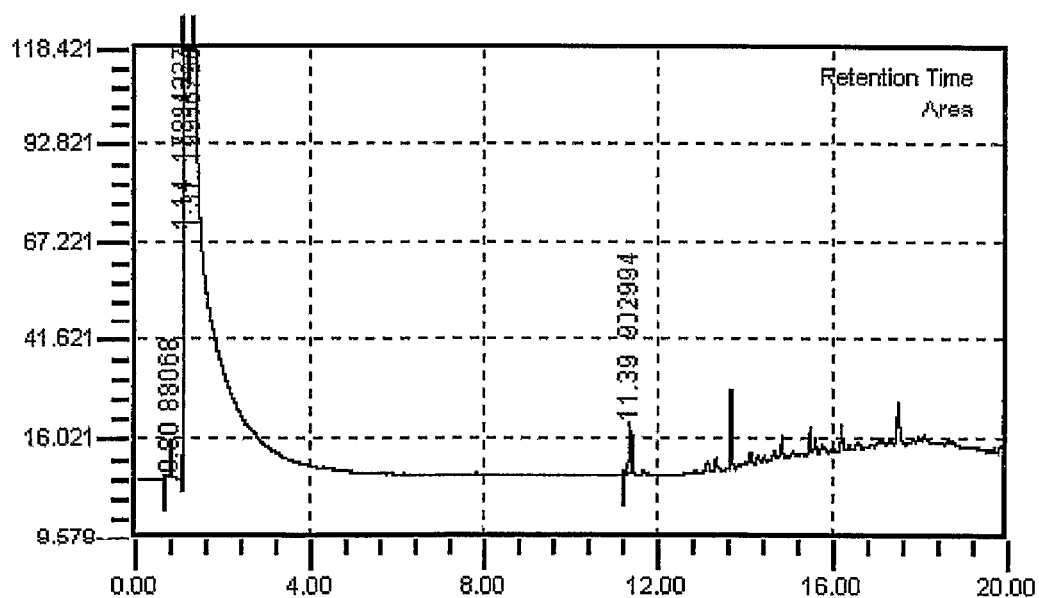
FIG. 12 is a GC chromatogram showing a concentration of PCP of timber after treating with microbes according to an embodiment of the invention, for 50 days.
Figure 13:
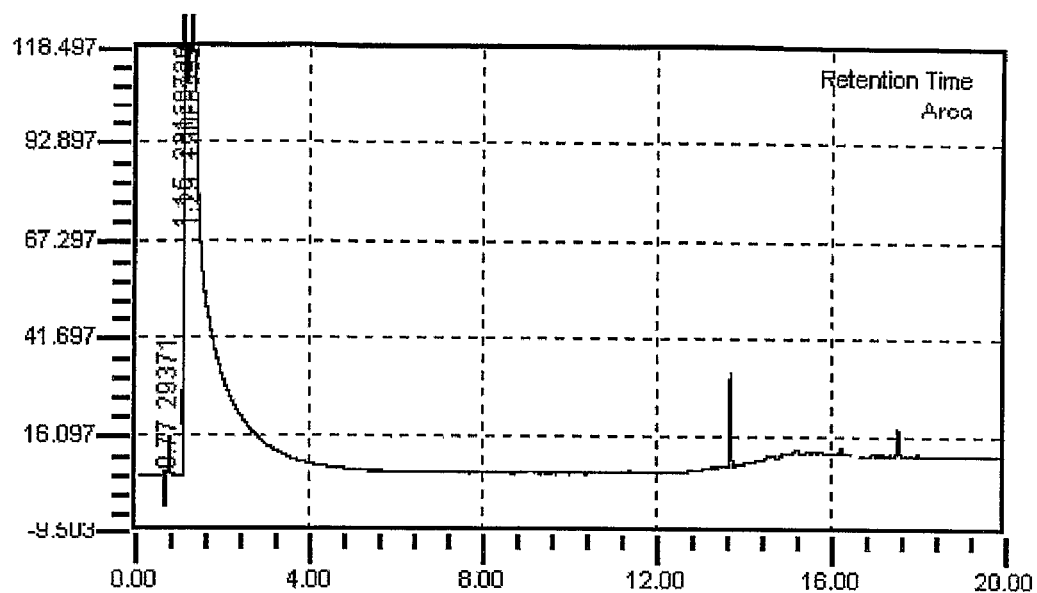
FIG. 13 is a GC chromatogram showing a concentration of PCP of reaction water after treating with microbes according to an embodiment of the invention, for 50 days.

5 tons of ammunition wooden boxes+microbial strains+ subterranean water a plan of the plant: a reactor where 0.5~1 ton of boards with original shape of an ammunition box are fixed was prepared, and then it was designed and run for pentachlorophenol (PCP) of timbers to be degraded according to circulation of the reaction water (subterranean water+ microbial strains). The reaction water was controlled to be 3.8~4 tons using subterranean water.

treatment period: 30~50 days treatment efficiency: timbers for ammunition boxes stacked in a large amount in an army have been deposited in 5% pentachlorophenol solution and used in order to prevent corrosion, and concentration of PCP on the surface of the timbers are uneven due to long exposure. In order to check effect of PCP degradation by a strain consortium, PCP degradation efficiencies for the degradation by indigenous microbes (Comparative example 8) and the degradation by bacterial consortium composed of EBC1000, Tnh, Pcpts, Djhc (Example 11) were measured. As a result, in the case of Example 11, 99.99% or more of pentachlorophenol was decomposed by a treatment using the circulation of the reaction water. Further, little pentachlorophenol was detected in the reaction water. By using this treatment, timbers for ammunition boxes contaminated with high concentration of pentachlorophenol can be regenerated into the original shape.

result: the representative results of treatment of five tons of timbers contaminated with pentachlorophenol were shown in the Tables 11 and 12, and FIGS. 11 to 13. Table 12 shows physicochemical condition of the reaction water.

TABLE 11

| | Timber of Comparative example 8 (1 kg) | | Original timber for ammunition boxes of Example 11 (540 kg): EBC100, EBC101, EBC103, EBC106, EBC107, Tnh, Pcpts, Djhc | |
|---|---|---|---|---|
| Treatment period (day) | PCP (mg/kg) | Number of indigenous microbes (cfu/ml) | PCP (mg/kg) | Number of inoculated microbes (cfu/ml) |
| 0 | 3000~10000 | $1.0 \times 10^4$ | 3000~10000 | $2.0 \times 10^6$ |
| 16 | | | 260~450 | $8.0 \times 10^6$ |
| 25 | | | 64~172 | $7.5 \times 10^7$ |
| 30 | 1300~8000 | | 23~32 | $6.0 \times 10^7$ |
| 50 | 1000~5000 | $2.5 \times 10^4$ | 16 | $3.0 \times 10^6$ |

TABLE 12

| Treatment period (day) | Temperature (°C.) | Dissolved Oxygen (mg/l) | Electric Conductivity (us/cm, specific) | Salinity (ppt) | pH | Chloride (mg/l) |
|---|---|---|---|---|---|---|
| 0 | 20.3 | 0.1~10.0 | 394 | 0.2 | 6.6 | 83 |
| 16 | 18.3 | 2.5~8.8 | 520 | 0.3 | 6.9 | 132 |
| 25 | 21.8 | 2.4~8.1 | 507 | 0.2 | 7.0 | 120 |
| 30 | 22 | 2.5~8.4 | 502 | 0.2 | 7.1 | 130 |
| 50 | 21 | 2.3~8.5 | 509 | 0.2 | 7.1 | 131 |

As shown in the above tables, although a part of PCP was decreased due to the decomposition by indigenous microbes in the Comparative example 8, the decomposition efficiency was very low. On the contrary, the strains constituting the EBC and Tnh, Pcpts, and Djhc constituting the NBC 2000 showed more effective decomposition efficiency due to mutual interaction with indigenous microbes.

Meanwhile, FIG. 11 is a GC chromatograph for initial PCP concentration, and FIG. 12 is a GC chromatograph, which measured PCP concentration of timber after treatment with strains of Example 11 for 50 days, and FIG. 13 is a GC chromatograph, which measured PCP concentration of reaction water after treatment with strains of Example 11 for 50 days.

As shown in the above Figs., although the initial concentration of pentachlorophenol in timber of ammunition boxes was very high (at 11.44 min. of FIG. 11), little pentachlorphenol (10~20 ppm) was detected in the timber after microbial reaction for 50 days (at 11.39 min. of FIG. 12) and no pentachlorophenol was detected in the reaction treatment water with which the boards were reacted.

Experimental Example 3

Biodegradation Treatment of Petroleum-Tar Acid

Swedish Petroleum-Tar Acid 3 kg+Luria-Bertani Liquid Medium+Microbial Strains+Minimal Liquid Medium 1 g of 100% petroleum-tar acid comprising [42,600 mg/kg TPH (total petroleum hydrocarbons), 190 mg/kg PAH (polycyclic aromatic hydrocarbon), 3.76 mg/kg BTEX (benzene, toluene, ethylbenzene, xylene), 0.33 mg/kg benzene, ethylbenzene <0.05 mg/kg, toluene <0.05 mg/kg, xylene 0.59 mg/kg, EOX (extractable organic halogens) 76.5 mg/kg, POX (purgeable organic halogens) 61.8 mg/kg, halogenated hydrocarbons <0.01 mg/kg, chloro-benzene <0.1 mg/kg, chloro-phenol <0.1 mg/kg, PCBs <0.01 mg/kg, cyanide <0.01 mg/kg, arsenic 0.76 mg/kg, lead 933 mg/kg, cadmium 0.14 mg/kg, mercury 0.66 mg/kg, sulfur 1.8%, pH 1.2] was mixed with 50 ml of sterilized Luria-Bertani liquid medium (10 g bacto-tryptone, 5 g bacto yeast extract, 10 g NaCl/1 liter desalted water), and pH is adjusted to be 8 using $Na_4OH$. Then, BS100, SP300, Tnh, EBC106, Aeng17, Aeng18, Bs101, and Nz2001 strains among NBC2000 strains were inoculated into the medium at the concentration of $10^5$/ml. On 50 and 70 days, nitrogen and phosphorus were added using 20 ml of minimal liquid medium. At 90, 100, 120, and 130 days, 20 ml of desalted water was added at each day. As a result, while little degradation was detected in the case of inoculating individual strains solely, significant degradation efficiency was shown in the case of inoculating combination of two or more strains. The result of the treatment with combination of all strains above except for Nz2001 and the result of the treatment with combination of all strains above were shown in the following table.

TABLE 13

| Treatment period (day) | Comparative example 9: Strains inoculated: BS100, SP300, Tnh, EBC106, Aeng17, Aeng18, Bs101, Ntar1, W24 (CFU/ml) | Example 12: Strains inoculated: BS100, SP300, Tnh, EBC106, Aeng17, Aeng18, Bs101, Ntar1, W24, Nz2001 (CFU/ml) | Analysis of total organic carbon (TOC) |
|---|---|---|---|
| 0 | $8.0 \times 10^5$ (Aeng17, Aeng18), $5.3 \times 10^7$ (Tnh) | $8.0 \times 10^5$ (Aeng17, Aeng18), $5.3 \times 10^7$ (Tnh) | |
| 15 | $7.0 \times 10^4$ (Aeng17, Aeng18), $5.3 \times 10^6$ (Tnh) | $1.2 \times 10^8$ (Aeng17, Aeng18) | |
| 74 | $1.0 \times 10^5$ (Aeng17, Aeng18), $1.2 \times 10^7$ (Tnh) | $1.1 \times 10^8$ (Tnh) | |
| 140 | $1.0 \times 10^5$ (Aeng17, Aeng18), $1.2 \times 10^7$ (Tnh) | $4.8 \times 10^7$ | Total carbon (TC): 4,500 mg/l Total organic carbon (TOC): 4,000 mg/l Total inorganic carbon (TIC): 500 mg/l |

As shown in the above Table, Aeng 17 and Aeng 18 strains were increased by 1,000 times, and Tnh was also increased by 10 times. Petroleum-tar acid, which was completely dissolved in the Luria-Bertani liquid medium, completely was decomposed by the metabolism of NBC2000 strains to vaporize the metabolites into carbon dioxide. Because petroleum-tar acid is a conglomerated mass composed of 20 kinds or more of various contaminants, it is very troublesome to individually determine the efficiency of treatment of each contaminant. Thus, in this experimental example, degradation efficiency was determined through calculation of total amount of carbon. This determination is accomplished by comparing the amount of all input carbon (petroleum-tar acid+medium+strains) with the amount of final remained carbon and calculating the amount of carbon delivered from petroleum-tar acid to bacterial strains. The amount of carbon in petroleum-tar acid was 45~50 mg, and total amount of carbon determined after treatment with the strains for 140 days was 4,500 mg/l. Thermodynamically verifying calculation is as follows:

Thermodynamically Verifying Calculation:

Total amount of input carbon (A): about 650 mg→total amount of output carbon (B): about 675 mg A: total amount of carbon of hazardous material contained in 1 g of input petroleum-tar acid: 45~50 mg+the amount of carbon of Luria-Bertani liquid medium: about 650 mg=total about 700 mg B: measured total amount of carbon (TC) is 4,500 mg/l, desalted water 80 ml+minimal liquid medium 40 ml+Luria-Bertani liquid medium 50 ml=170 ml–10 ml~20 ml (vaporized amount)=160 ml, the amount of carbon calculated on the basis of the TC is 720 mg (160:x=1000:4500).

It can be seen that input amount of carbon was corresponding to output amount of carbon from the above calculation (small error is a experimental error). That is, in the Table 13, the increase of microbial strains as time goes by means that the microbes proliferated using the petroleum-tar acid as a carbon source. Petroleum-tar acid is a solid, which is naturally insoluble to water. Accordingly, the petroleum-tar acid is not completely soluble without metabolism of petroleum-tar acid decomposing strains, and it is required to use LB as a nutrition-aiding catalyst to accelerate the dissolving and decomposing rates. It is often to input oxygen, nutrition additives, and microbial strains to achieve bioaugmentation in an actual environment.

Most of microbial strains cannot grow in nutritive medium comprising petroleum-tar acid having high concentration of complex toxic substances or high concentration of petroleum-tar acid. However, it was shown that the NBC2000 strain according to the invention was activated using petroleum-tar acid as a carbon source, wherein petroleum-tar acid and a nutrition-aiding catalyst are present.

In addition, in Comparative example 9 treated by the remaining strains except for the Nz2001 strain, the numbers of microbial strains were little increased. However, in Example 12 treated by the total strains comprising the Nz2001 strain, the microbial strains were significantly increased. This proves that the Nz2001 strain is sulfur strain utilizing 1.8% (18 mg) of high concentration of sulfur contained in the petroleum-tar acid as sources of metabolism of amino acid and energy.

In order to support the above results, the inventor carried out the following experiments. It was again confirmed that the microbes grew and dominant strains of Tnh, Aeng 17, and Aeng18 were increased by 10~100 times by mixing minimal liquid medium other than LB, tap water and sterile distilled water with petroleum-tar acid.

1 g of 100% petroleum-tar acid was added to 50 ml of sterilized minimal liquid medium (0.65 g $K_2HPO_4$, 0.17 g $KH_2PO_4$, 0.5 g $NaNO_3$, 0.1 g $MgSO_4.7H_2O$/1 liter desalted water), 50 ml tap water and 50 ml sterile distilled water, respectively, and the respective mixture were aerobically shaken. After mixing in 50 ml, pH was adjusted to be 8 using $Na_4OH$. And then, BS100, Sp300, Tnh, EBC106, Aeng17, Aeng18, Bs101, Nz2001 strains of the NBC2000 strain were inoculated in an amount of $10^4$~$10^7$/ml, and aerobically shaken at 30° C. and 100 rpm for 55 days. The results were shown in Examples 13 (minimal liquid medium), 14 (tap water) and 15 (sterile distilled water) of Table 14.

As can be seen from the Table 14, the strains according to the invention were proliferated even in the experiments wherein the strains were inoculated into minimal liquid medium having no carbon sources except the petroleum-tar acid. This means that the strains used petroleum-tar acid as a carbon source.

Experimental Example 4

Biodegradation of PCE

PCE+Minimal Liquid Medium+Microbial Strains+Oxygen ($O_2$)

To verify the biodegradation of perchloroethylene (PCE), 193.8 ml of the minimal liquid medium (0.65 g $K_2HPO_4$, 0.17 g $KH_2PO_4$, 0.5 g $NaNO_3$, 0.1 g $MgSO_4.7H_2O$/1 liter desalted water) was put into a gas experimental apparatus. The apparatus was covered up tight, sterilized and allowed to cool. And then, EBC 106, 107 strain and Tnh strain were inoculated in an amount of $10^5$ cfu/ml (Example 16). And then, 6.2 ml PCE was added to be about 50,000 ppm. Solubility of PCE is 0.015 g/100 ml water (150 mg/liter, 25° C.), un-dissolved PCE settles down under the water.

The PCE was not flown out of the bottle and subject to biodegrading under an aerobic state by using oxygen inside of the bottle and oxygen separately and periodically (24 hours unit) supplied from an exterior. Carbon dioxide ($CO_2$) generated by a biodegradation activity of microbes in the bottle was removed with KOH in an experimental apparatus connected to the bottle ($CO_2+2KOH \rightarrow K_2CO_3+H_2O$). Nitrogen ($NO_3$—N) and phosphorous ($PO_4$—P) were added in a ratio of 3:1 every 3~8 days to accelerate the activity of microbes. To contrast this, Tnh only was inoculated in an amount of $10^5$ cfu/ml and decrease of PCE was observed as time goes by. As a result of that, when individual strain solely was inoculated, a part of PCE was decomposed. However, when the combination of two or more strains was inoculated, the decomposition efficiency was satisfactory. When all strains were combined and inoculated, the decomposition efficiency was most excellent. Representative examples were shown in Table 15 and FIGS. 14 to 16.

TABLE 14

| Treatment period (day) | Example 13: an analysis of inoculated strains: BS100, SP300, Tnh, EBC106, Aeng17, Aeng18, Bs101, Nz2001 (CFU/ml) | Example 14: an analysis of inoculated strains: BS100, SP300, Tnh, EBC106, Aeng17, Aeng18, Bs101, Nz2001 (CFU/ml) | Example 15: an analysis of inoculated strains: BS100, SP300, Tnh, EBC106, Aeng17, Aeng18, Bs101, Nz2001 (CFU/ml) |
|---|---|---|---|
| 0 | $5.3 \times 10^7$ (Tnh) $1.8 \times 10^5$ (EBC106) $9.0 \times 10^5$ (Aeng17, Aeng18) | $5.3 \times 10^7$ (Tnh) $1.8 \times 10^5$ (EBC106) $9.0 \times 10^5$ (Aeng17, Aeng18) | $5.3 \times 10^7$ (Tnh) $1.8 \times 10^5$ (EBC106) $9.0 \times 10^5$ (Aeng17, Aeng18) |
| 15 | $8.0 \times 10^6$ (Tnh) $1.1 \times 10^5$ (EBC106) $8.0 \times 10^6$ (Aeng17, Aeng18) | $2.0 \times 10^6$ (Tnh) $1.1 \times 10^5$ (EBC106) $1.0 \times 10^6$ (Aeng17, Aeng18) | $2.0 \times 10^6$ (Tnh) $7.0 \times 10^4$ (EBC106) $1.6 \times 10^7$ (Aeng17, Aeng18) |
| 30 | $1.0 \times 10^7$ (Tnh) $3.0 \times 10^4$ (EBC106) $4.0 \times 10^7$ (Aeng17, Aeng18) | $1.3 \times 10^6$ (Tnh) $2.0 \times 10^4$ (EBC106) $3.3 \times 10^6$ (Aeng17, Aeng18) | $1.0 \times 10^5$ (Tnh) $3.0 \times 10^4$ (EBC106) $2.0 \times 10^6$ (Aeng17, Aeng18) |
| 55 | $2.5 \times 10^8$ (Tnh) $3.2 \times 10^4$ (EBC106) $3.0 \times 10^7$ (Aeng17, Aeng18) | $1.5 \times 10^8$ (Tnh) $4.0 \times 10^7$ (Aeng17, Aeng18) | $6.0 \times 10^7$ (Tnh) $7.0 \times 10^4$ (EBC106) $6.0 \times 10^7$ (Aeng17, Aeng18) |

TABLE 15

| Treatment period (day) | Example 16 Inoculated strains: EBC106, EBC107, Tnh | Concentration of PCE (mg/l) |
|---|---|---|
| 0 | 9.3 × 10$^5$ (EBC107), 1.7 × 10$^5$ (Tnh) | 50,000 |
| 5 | 9.2 × 10$^4$ (EBC107), 1.5 × 10$^3$ (Tnh) | |
| 8 | 9.0 × 10$^7$ (EBC107) | completely dissolved |
| 10 | 1.3 × 10$^7$ (EBC107), 2.6 × 10$^6$ (Tnh) | ND* |
| 16 | 7.0 × 10$^6$ | |
| 22 | 1.5 × 10$^6$ | |
| 30 | 3.0 × 10$^6$ | |

*ND: not detected

As shown in Table 15, the strains were adapted until 5 days and reduced by 10~100 times. In 8 days, 50,000 mg/liter of PCE was completely dissolved in the minimal liquid medium by microbial decomposition action, and all of PCE was decomposed around 10 days. The reason is that PCE deposited was dissolved by about 70% and KOH was almost dissolved around 7 days, PCE was completely dissolved on 8 days, and EBC107 and Tnh strains were increased by 1,000 times around 10 days. It was demonstrated that due to such mutual interactions of EBC and Tnh strains, PCE, which was difficult to aerobically be decomposed, was completely aerobically biodegraded for a short time even in a level of high concentrations according to the strains.

Figure 14:
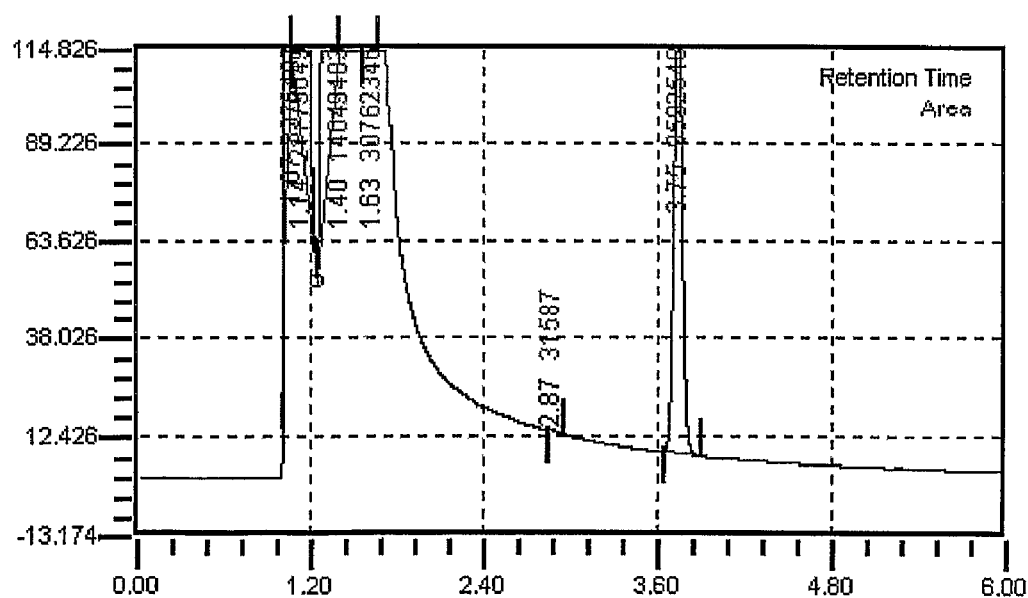
FIG. 14 is a GC chromatogram showing an initial concentration of PCE just before treating with microbes according to an embodiment of the invention.
Figure 15:
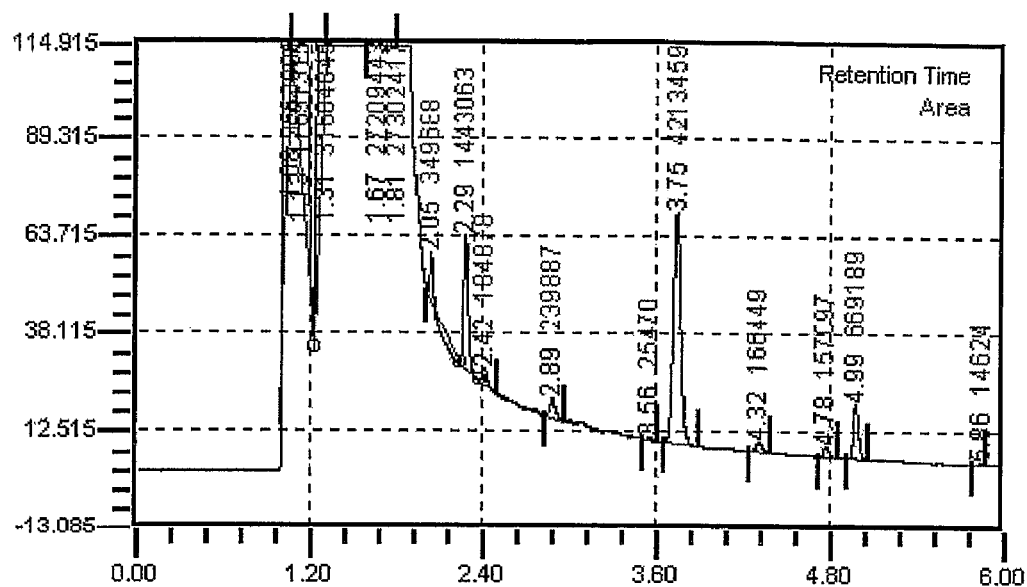
FIG. 15 is a GC chromatogram showing a concentration of PCE treated with an individual strain only.
Figure 16:
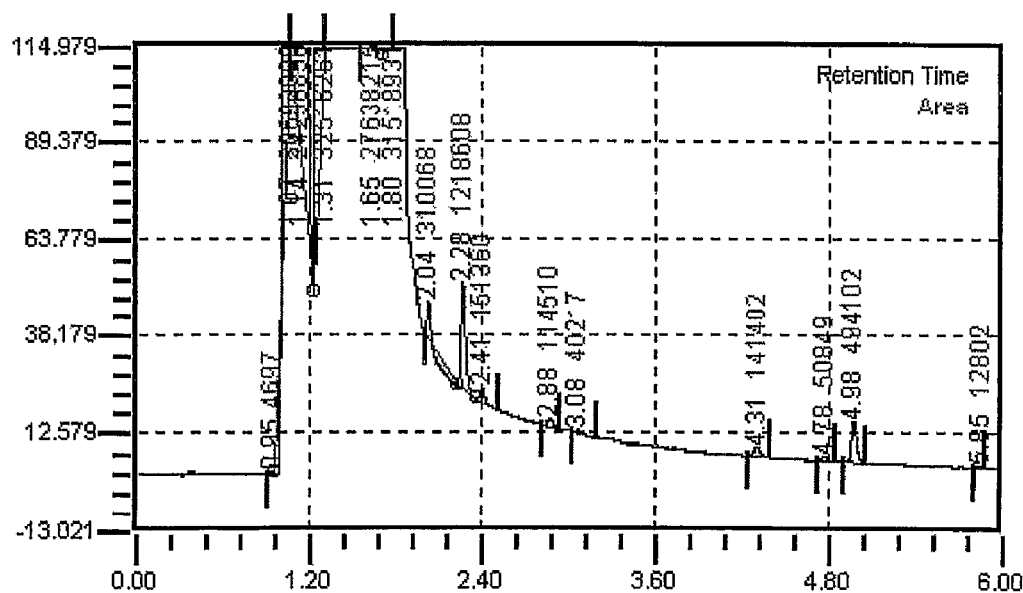
FIG. 16 is a GC chromatogram showing a concentration of PCE treated with microbes according to an embodiment of the invention.

FIG. 14 is a GC chromatograph showing initial concentration of PCE just before treatment with strains, FIG. 15 is a GC chromatograph showing concentration of PCE treated with sole strain only, and FIG. 16 is a GC chromatograph showing concentration of PCE treated with the whole strains.

The initial concentration of PCE in FIG. 14 and concentration of PCE of Comparative example in FIG. 15 were shown at 3.75 minutes, but in FIG. 16 treated with strains according to the invention, PCE was not shown at all at 3.75 minutes due to the biodegradation of microbes.

Experimental Example 5

Biodegradation of Toluene

Toluene+Minimal Liquid Medium+Microbial Strains+O$_2$ 150 ml of the minimal liquid medium (0.65 g K$_2$HPO$_4$, 0.17 g KH$_2$PO$_4$, 0.5 g NaNO$_3$, 0.1 g MgSO$_4$.7H$_2$O/1 liter desalted water) was put into 500 ml Erlenmeyer flask, sterilized and allowed to cool. And then, EBC strains and Nz2001 strains were inoculated into the medium. Then, 3 ml toluene was added to it, immediately sealed and then shaken at 25° C. and 110 rpm. Volatilization of toluene was blocked by double-seal. After 15 days, 3 ml toluene and strains were added. As a result of that, when treating with the sole strain only, the decomposition was not nearly achieved. However, when two or more strains were combined, satisfactory decomposition efficiency was shown. In particular, when treating with EBC strains+(added Aeng17+Aeng18+W24), EBC strain+Nz2001+(added Aeng17+Aeng18+W24), excellent decomposition efficiency was shown. Representative results were shown in below Table 16 and FIGS. 16 to 18.

EBC strains+(added Aeng17+Aeng18+W24): toluene was volatilized and disappeared around 29 days.

EBC strains+Nz2001+(added Aeng17+Aeng18+W24): toluene was volatilized and disappeared around 36 days.

TABLE 16

| Treatment period (day) | Example 17 initial inoculated strains + (added inoculated strains): EBC106, EBC107, EBC108 + (Aeng17 + Aeng18 + W24) (cfu/ml) | Example 18 initial inoculated strains + (added inoculated strains): EBC106, EBC107, EBC108 + Nz2001 + (Aeng17 + Aeng18 + W24) (cfu/ml) |
|---|---|---|
| 0 | 5.3 × 10$^4$ | 2.0 × 10$^4$ |
| 10 | 4.0 × 10$^2$ (EBC106, EBC108) | 3.0 × 10$^2$ (EBC106, EBC108) |
| 15 | 6.0 × 10$^6$ additionally inoculated | 6.0 × 10$^6$ additionally inoculated |
| 30 | 1.3 × 10$^7$ (EBC106, EBC108) | 3.0 × 10$^2$ (EBC106, EBC108) |
| 36 | 7.0 × 10$^6$ (EBC106, EBC108) | 7.0 × 10$^2$ (EBC106, EBC108) |
| 37 | 1.0 × 10$^6$ (EBC106, EBC108) | 1.0 × 10$^7$ (EBC106, EBC108) |
| 41 | 6.5 × 10$^6$ (EBC106, EBC108) | 2.0 × 10$^6$ (EBC106, EBC108) |

It was carried out that toluene was subject to decomposing by initially inoculating EBC106, 107 and 108 and Nz2001 in an amount of 10$^4$ cfu/ml, respectively. However, EBC106 and 108 strains only appeared, and thus it was proved that EBC106 and 108 acted as dominant species for toluene. When initially inoculating EBC strain only, all toluene was disappeared around 29 days, and EBC106 and 108 strains were increased by 100,000 times. Also, even when EBC strain and Nz2001 were inoculated together at an initial stage, EBC 106 and 108 strains were increased by about 100,000 times after toluene was disappeared around 36 days. The reason of significant increases of EBC106 and 108 after 40,000 ppm (mg/ml) of toluene was disappeared is evidence that the strains are dominant species using toluene as a main carbon source. It was again confirmed that the activities of EBC106 and 108 strains were greatly increased due to mutual interactions of EBC strains and NBC2000 strains.

Figure 17:
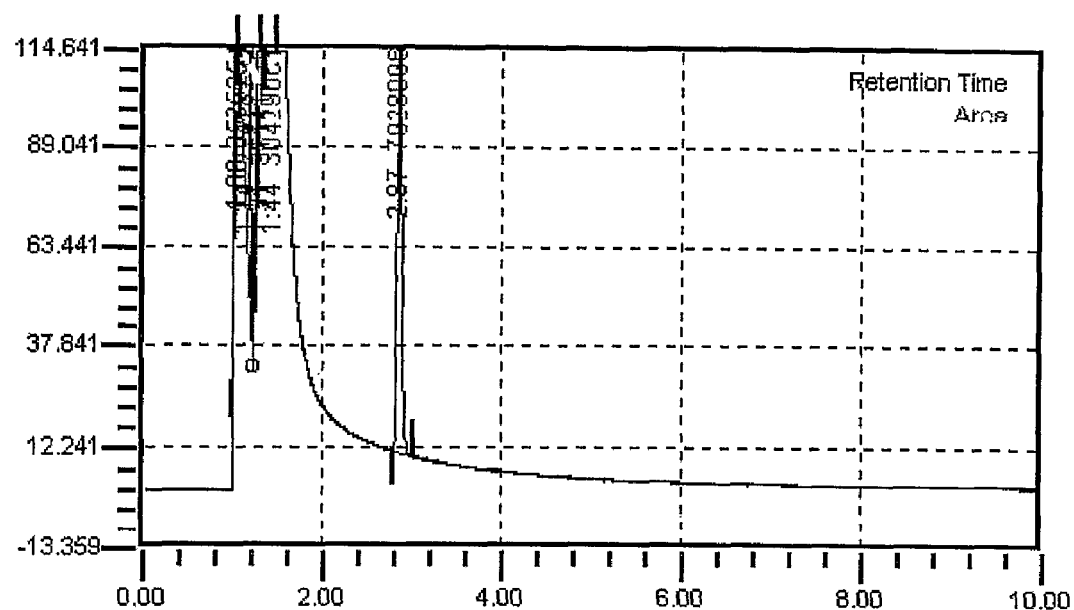
FIG. 17 is a GC chromatogram showing an initial concentration of toluene just before inputting microbes according to an embodiment of the invention.
Figure 18:
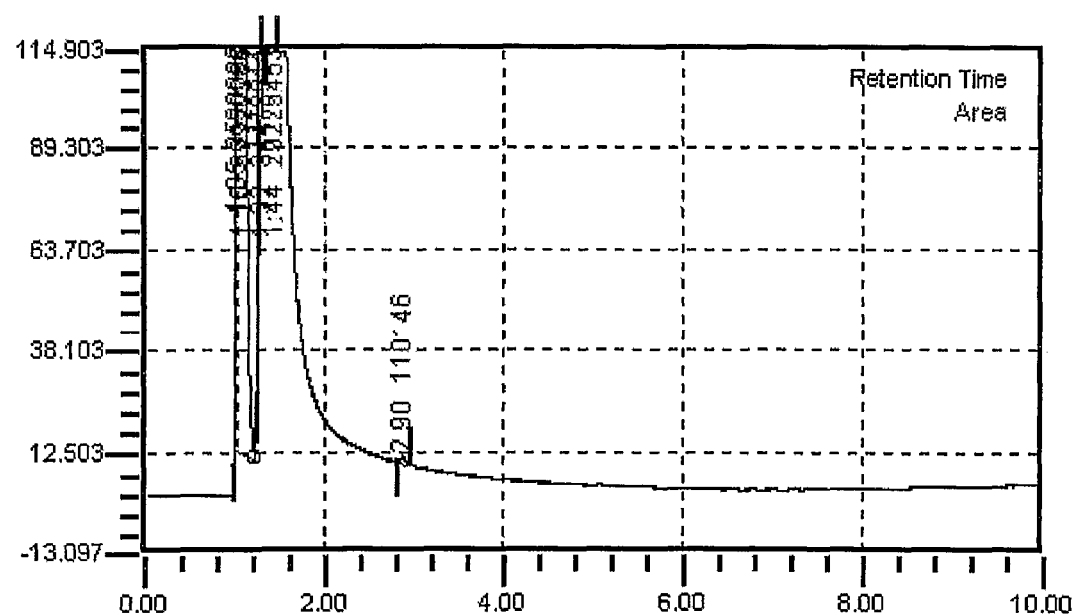
FIG. 18 is a GC chromatogram showing a concentration of toluene treated with microbes according to an embodiment of the invention, for 41 days.

FIG. 17 is a GC chromatograph showing initial concentration of toluene just before inputting strains; FIG. 18 is a GC chromatograph showing concentration of toluene after treating strains for 41 days. As shown in Figs., the initial concentration of toluene shown at 2.87 minutes in FIG. 17 was slightly detected at 2.9 minutes in FIG. 18 after treatment with strains. That is, it was again confirmed that most of toluene was biodegraded.

Experimental Example 6

Treatments of Bacterial Consortium NBC2000 and Bacterial Consortium EBC1000

Bacterial consortium NBC2000 and/or EBC1000 strains were inputted in a consortium unit to confirm biodegradation of endocrine disrupters.

Cyprus soil polluted with PCBs was tested under the same condition as the Experimental example 1. 2). 26 kinds of strains consisting of the NBC2000 were inputted into an experimental group in an amount of 10$^5$~10$^6$ cfu/ml and the NBC2000 consortium and the EBC1000 consortium were inputted into another experimental group in an amount of 10$^4$~10$^6$ cfu/ml, respectively, for 113 days.

Swedish soil polluted with PCP and dioxin was treated with an experimental group in which 26 kinds of strains consisting of the NBC2000 were inputted in an amount of 10$^5$~10$^6$ cfu/ml for 92 days and with another experimental group the NBC2000 consortium and the EBC1000 consortium were inputted in an amount of 10$^4$~10$^6$ cfu/ml for 200 days, under the same condition as the Experimental example 2.

PCE was tested under the same condition as the Experimental example 4, toluene was treated under the same condition as the Experimental example 5 and petroleum-tar acid was treated under the same condition as the Experimental example 3, with an experimental group in which 26 kinds of strains consisting of the NBC2000 were inputted in an amount of $10^5 \sim 10^6$ cfu/ml, and in another experimental group in which the NBC2000 consortium and the EBC1000 consortium were respectively inputted in an amount of $10^4 \sim 10^6$ cfu/ml, for 35, 45 and 140 days, respectively.

As a result, it was shown that each of endocrine disrupters was effectively decomposed. Specific results were shown in Table 17.

organic carbon as their supernatant was measured by a TOC analyzer (High TOC II+N by Elementar Analysensysteme GmbH).

3) Gas Chromatography (GC) Analysis

Soil and liquid samples of each group were taken every each measuring times and pre-treated. And, the change of toxic substances was quantitatively analyzed according to operational guides of Donam GC (DS6200) and gas chromatograph (GC2010, Gas Chromatograph, Shimadzu) published by Shimadzu. Standard examination of PCP in Swedish and New Zealand soils was carried out by using Zebron (ZB)-5 7HM-G002-11 column (30 m×30 mm×25 μm) in GC2010, based on retention time 12.52~12.55. Standard

TABLE 17

| | | Combination of strains | | | |
|---|---|---|---|---|---|
| object to be treated/ treatment period | | Example 19 (NBC2000) | | Example 20 (NBC2000 + EBC1000*) | |
| Endocrine disrupters | Treatment period (day) | Concentration before treatment | Concentration after treatment | Concentration before treatment | Concentration after treatment |
| Soil with PCBs | 113 | 700~1000 mg/kg | 35 mg/kg | 700~1,000 mg/kg | 15 mg/kg |
| Soil with PCP | 92 | 50,000 mg/kg | 82 mg/kg | 50,000 mg/kg | 49 mg/kg |
| Soil with dioxin | 200 | 2,500 ng/kg | 86 ng/kg | 2,500 ng/kg | 86 ng/kg |
| PCE | 35 | 50,000 mg/l | 20 mg/l | 50,000 mg/l | ND** |
| Toluene | 45 | 40,000 mg/l | 30 mg/l | 40,000 mg/l | 10 mg/l |
| Petroleum-Tar acid | 140 | *** | 99% biodegradation | *** | 99% biodegradation |
| Soil with petroleum oil: in situ Bioremediation of 470 tons soil | 60 | TPH: 500~700 mg/kg BTEX: 200~400 mg/kg | TPH: 10~60 mg/kg BTEX: 0.5~20 mg/kg | TPH: 500~700 mg/kg BTEX: 200~400 mg/kg | TPH: 5~20 mg/kg BTEX: 0.5~5 mg/kg |

*EBC1000 is a bacterial consortium consisting of EBC100, 101, 103, 104, 105, 106, 107, 108 and 109, is provided in Korean Patent Registration No. 284313, U.S. Pat. No. 6,383,797, Australia Patent No. 759338 and New Zealand Patent No. 517647 and internationally deposited (KCTC 0652 BP).
**ND: not detected
*** Comprising TPH (total petroleum hydrocarbons) 42,600 mg/kg, PAH (polycyclic aromatic hydrocarbon) 190 mg/kg, BTEX (benzene, toluene, ethylbenzene, xylene) 3.76 mg/kg, benzene 0.33 mg/kg, ethylbenzene <0.05 mg/kg, toluene <0.05 mg/kg, xylene 0.59 mg/kg, EOX (extractable organic halogens) 76.5 mg/kg, POX (purgeable organic halogens) 61.8 mg/kg, halogenated hydrocarbons <0.01 mg/kg, chloro-benzene <0.1 mg/kg, chloro-phenol <0.1 mg/kg, PCBs <0.01 mg/kg, cyanide <0.01 mg/kg, arsenic 0.76 mg/kg, lead 933 mg/kg, cadmium 0.14 mg/kg, mercury 0.66 mg/kg, sulfur 1.8%.

7. An Experimental Analysis Method

This analysis was carried out, based on fair test methods of water pollution (Notification No. 2001-53 of Ministry of Environment), wastes (Notification No. 2002-112 of Ministry of Environment), soil pollution (Notification No. 2002-122 of Ministry of Environment) and standards methods (APHA-AWWA-WEF, $18^{th}$ & $20^{th}$ ed.)

1) Colony Forming Unit (CFU)

According to microbe-examination method of standard methods, colonies of indigenous microbes and inoculated microbes consortiums were examined by a plate count method and it was checked that the microbes were proliferated due to a decrease of toxic substances at an initial stage and as time goes by.

2) Total Organic Carbon (TOC)

According to standard methods, undiluted solution and samples at each measured time were centrifuged. And, total examination of PCP in timber of ammunition boxes measured by a gas chromatography of Donam Instrument (DS6200 Gas Chromatograph, dsCHROM) was carried out by using Zebron (ZB) 624 7HK-G005-36 column (30 m×53 mm×3 μm), based on retention time 11.39~11.44. PCE and toluene were measured based on retention time 3.75 and 2.87~2.90, respectively.

4) GCMS Analysis

Soil and liquid samples of each group were taken every each measuring times and pre-treated. And, the change of toxic substances was analyzed regarding their concentrations and molecular structures by a GCMS (GCMS QP5050A-Shimadzu Co.) database according to a GCMS operational guide published by Shimadzu and DB-5 ms (Ca. No. 1225532) column and helium gas were used.

5) Pre-Treatment for Quantitative Analysis of Toxic Substances

Pre-treatment for quantitatively analyzing the decrease of toxic compound substances by a bacterial consortium was carried out according to standard methods. Extraction manner for main chlorine compounds was applied together with the provisions of Korean Patent Registration No. 284313.

As explained above, since the bacterial consortiums according to the invention consists of novel wild strains separated from an ecosystem and effectively decomposes organic-chlorinated compounds such as polychlorinated biphenyl, dioxin, pentachlorophenol, PCE, PAH and petroleum-tar acid, and toluene which are all endocrine disrupters by using them as carbon sources, they can purify and restore the soils, wastes, water and atmosphere polluted with the endocrine disrupters by an environmental-friendly method. Accordingly, the bacterial consortiums according to the invention can effectively prevent a contamination of toxic substances, which are difficult to treat, and restore en environment of sites, which was polluted in a large scale. In addition, since the bacterial consortiums according to the invention can be used in an aerobic manner, organic-chlorinated compounds such as polychlorinated biphenyl, dioxin, and PCE, etc., petroleum-tar acid, which are all known as substances being unable to biologically treat, PCP, PAH, toluene which can be partially biodegraded, are mostly biodegraded with inexpensive costs and convenient processes, so that the soils, wastes, subterranean water and atmosphere polluted with them can be easily restored.

[Indications Relating to Deposited Microorganism or Other Biological Material]

What is claimed is:

1. A biologically pure culture of bacterial consortium NBC 2000, identified by Accession No. KCTC 10623BP, comprising *Pseudomonas* sp. Cy100 strain, *Serratia* sp. Aeng18 strain, *Pseudomonas* sp. Djhc strain, *Pseudomonas* sp. Ntar3 strain, *Serratia* sp. Ntar2 strain, *Pseudomonas* sp. EBC107 strain, *Pseudomonas aeruginosa* Tnh strain, *Aeromonas hydrophila* Aeng17 strain, *Pseudomonas aeruginosa* Pcpts strain, *Stenotrophomonas maltophilia* Ntar1 strain, *Pseudomonas aeruginosa* Sp300 strain, *Chryseomonas luteola* Gc501 strain, *Chryseomonas* sp. Gc500 strain, *Chryseomonas luteola* Gc300 strain, *Brevundimonas vesicularis* Cy101 strain, *Brevundimonas vesicularis* Cy102 strain, *Brevundimonas vesicularis* Cy103 strain, *Bacillus stearothermophilus* Bs100 strain, *Bacillus stearothermophilus* Cy104 strain, *Bacillus* sp. Cy105 strain, *Bacillus* sp. Cy106 strain, *Bacillus* sp. Cy107 strain, *Bacillus cereus* EBC106 strain, Bs101 strain which is petroleum-tar acid decomposition gram-positive bacteria, Nz2001 strain which is sulfur strain and W24 strain which is oil decomposition gram-negative bacteria.

* * * * *